United States Patent [19]

Haase

[11] Patent Number: 4,668,273

[45] Date of Patent: May 26, 1987

[54] QUATERNARY AMMONIUM SALTS OF DIEPOXIDES AND DIAMINES, THEIR PREPARATION AND USE

[75] Inventor: Jaroslav Haase, Riehen, Switzerland

[73] Assignee: Ciba-Geigy Corporation, Ardsley, N.Y.

[21] Appl. No.: 422,994

[22] Filed: Sep. 24, 1982

Related U.S. Application Data

[62] Division of Ser. No. 188,431, Sep. 19, 1980, abandoned.

[30] Foreign Application Priority Data

Sep. 20, 1979 [CH] Switzerland ............... 8489/79

[51] Int. Cl.$^4$ ............ A61K 31/74; A01N 43/40; A01N 9/20; C07D 211/30
[52] U.S. Cl. ........................... 71/67; 71/94; 424/78; 546/190
[58] Field of Search ............ 71/67, 94; 546/190; 424/78, 267

[56] References Cited

U.S. PATENT DOCUMENTS 3,324,176  6/1967  Kirschnek et al. ............ 564/59

FOREIGN PATENT DOCUMENTS 2000164A  1/1979  United Kingdom .
1546809   5/1979  United Kingdom .

Primary Examiner—Leonard Schenkman
Assistant Examiner—Joseph A. Lipovsky
Attorney, Agent, or Firm—Edward McC. Roberts; Joseph G. Kolodny

[57] ABSTRACT

The invention relates to processes for the treatment of substrates which comprise applying at least one ammonium salt to the substrate as an algicide, bactericide or fungicide, said ammonium salt containing units which contain diepoxide and diamine radicals.

7 Claims, No Drawings kyl, halogenoalkyl, hydroxyalkyl or alkoxy, D is a divalent bridge member of one of the formulae $$-NHCONH-, \quad (1.7)$$

$$-NHCOD_1CONH-, \quad (1.8)$$

$$-CONH-, \quad (1.9)$$

$$-OCONH-, \quad (1.10)$$

$$-COO-, \quad (1.11)$$

$$-COD_2CO-, \quad (1.12)$$

(1.13)

or

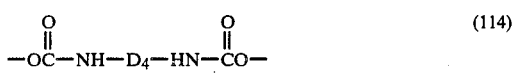

(1.14)

in which $D_1$ is a direct bond, alkylene, alkenylene, arylene, heteroarylene, diaminoalkylene, diaminoarylene or unsubstituted or halogen-substituted dioxyalkylene, polyoxyalkyleneoxy or dioxyarylene, $D_2$ is diaminoalkylene or unsubstituted or halogen-substituted dioxyalkylene, polyoxyalkyleneoxy or dithioalkylene, $D_3$ is arylene and $D_4$ is alkylene or arylene, $T_1$, $T_2$ and $T_3$ are each hydrogen or methyl, $X_1$, $X_2$, $X_3$ and $X_4$ are each $-COO-$, $-OOC-$, $-O-$ or a direct bond and $A_1$ and $A_2$ are each a heterocyclic ring which has 5 or 6 ring members and 2 nitrogen atoms and can be substituted by alkyl, or alkylene which can be interrupted by hetero-atoms, or cycloalkylene, cycloalkenylene, arylene or aralkylene which have 1 or 2 rings and can be substituted by alkyl or halogen, the bridge members in ring form being bonded via a direct bond, via a hetero-atom or via an alkylene bridge, which can be interrupted by hetero-atoms.

The process for the preparation of these ammonium salts and their use as a cosmetic, as washing agents for textile materials dyed or printed with cationic dyes, as paper sizes, as fixing agents for cellulose-containing materials dyed with anionic dyes and as algicides, fungicides and bactericides constitute further subjects of the present invention. Amongst the manifold applications, the use of the ammonium salts according to the invention as a cosmetic and in particular as a hair cosmetic is of primary interest. The diverse possibilities for use of the ammonium salts are an important advantage of the present invention.

The radicals $R_1$, $R_2$, $R_3$ and $R_4$ in the cationic units of the quaternary ammonium salts of the formula (1) are, inter alia, straight-chain or branched alkyl radicals having 1 to 8 carbon atoms, for example methyl, ethyl, propyl, isopropyl, butyl, isobutyl, tert.-butyl, hexyl, octyl, isooctyl or tert.-octyl.

Preferred alkyl radicals are those having 1 to 4 carbon atoms and in particular methyl and ethyl.

Substituted alkyl radicals are, for example, hydroxyalkyl, cyanoalkyl, alkoxyalkyl or alkylthioalkyl, and the substituents alkoxy and alkylthio preferably have 1 to 4 and in particular 1 or 2 carbon atoms.

Cycloalkyl radicals $R_1$ to $R_4$ are essentially cyclopentyl or cyclohexyl, and these can be substituted in the same way as the alkyl radicals.

Alkenyl radicals $R_1$ to $R_4$ can contain 2 to 8 carbon atoms. Those having 2 to 4 carbon atoms are preferred.

Suitable radicals are the alkenyl radicals which correspond to the alkyl radicals mentioned. The substituents mentioned for the alkyl radicals can, in general, also be used for the alkenyl radicals.

Aryl and aralkyl radicals $R_1$ to $R_4$ are in particular phenyl and benzyl, which are unsubstituted or substituted by hydroxyl, cyano, halogen, carboxyl, alkyl, hydroxyalkyl, alkoxy or alkylthio, halogen being preferably iodine, fluorine or in particular bromine or chlorine, and alkyl, hydroxyalkyl, alkylthio and alkoxy having 1 to 4 and preferably 1 or 2 carbon atoms.

Furthermore, the two substituents on each nitrogen can form, together with the nitrogen atom to which they are bonded, a heterocyclic ring having 5 or 6 ring members. Examples of such heterocyclic rings are the thiomorpholine ring, preferably the morpholine, pyrrolidine or imidazoline ring and in particular the piperidine ring.

$Y_1$ and $Y_2$ in formula (1), which can be different from or preferably identical to one another, are, for example, the alkylene grouping of the indicated formula (1.6), in which m is an integer from 1 to 12 and preferably 1 to 6. When m is 1, i.e. in the case of the $-CH_2-$ grouping, the bond to the bridge member D must be made via atoms other than nitrogen and oxygen; in particular, the bond is via a carbon atom. Furthermore, the sum of the m's in the two groups of the formula (1.6) in $Y_1$ and $Y_2$ must be not less than 3. As already indicated by the formula (1.6), the alkylene radicals can be branched or straight-chain, the latter being preferred.

$Y_1$ and $Y_2$ can also be an aromatic bridge member, in particular a substituted or unsubstituted phenylene.

Possible substituents on these aromatic bridge members are as a rule lower alkyl, lower alkoxy, lower hydroxyalkyl or lower halogenoalkyl having 1 to 4 carbon atoms, hydroxyl and halogen, in particular chlorine or bromine.

The bridge member D in formula (1) corresponds to divalent radicals of one of the indicated formulae (1.7) to (1.14).

$D_1$ in formula (1.8) is, inter alia, a direct bond, or alkylene, for example having 1 to 12 carbon atoms. Specific groupings are $-CH_2-$, $-C_2H_4-$, $-C_3H_6-$, $-C_4H_8-$, $-C_5H_{10}-$ and $-C_6H_{12}-$, these groupings being branched or preferably straight-chain.

Alkenylene $D_1$ can be represented, for example, by the formulae $$-CH=CH- \quad (1.15)$$

or $$-CH=CH-CH=CH- \quad (1.16)$$

or also

(1.17)

and

(1.18)

If $D_1$ is arylene or heteroarylene, the corresponding aromatic bridge members can be represented, for example, by one of the formulae

QUATERNARY AMMONIUM SALTS OF DIEPOXIDES AND DIAMINES, THEIR PREPARATION AND USE

This is a division of application Ser. No. 188,431, filed Sept. 19, 1980, now abandoned.

Quaternary ammonium salts of diamines and dime- thylnaphthyl dihalides or dimethyldiphenyl dihalides have been disclosed in British Patent Specification No. 1,546,809, and quaternary ammonium salts of polyamines and aliphatic or aromatic dihalides have been disclosed in British Patent Application No. 2,000,164A. In contrast to these salts, the present invention describes novel quaternary ammonium salts of diamines and diepoxides, which are more readily accessible than the known ammonium salts of di- or poly-amines and dihalides, since diepoxides are products produced on a large scale in the plastics industry for the preparation of epoxide resins.

The present invention thus relates to quaternary ammonium salts which have, as the characterising feature, units which contain diepoxide and diamine radicals and have the formula

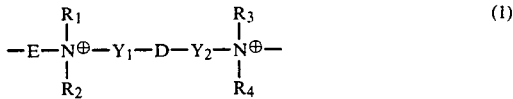

in which E is a divalent bridge member which has one of the formulae

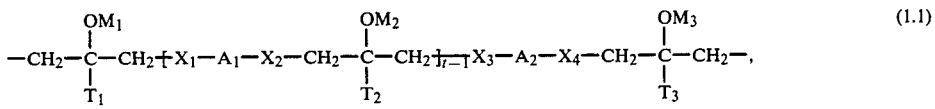

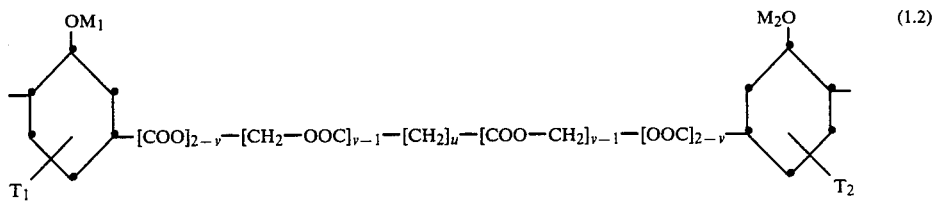

or

in which t is a number from 1 to 4, u is an integer from 1 to 8 and v is 1 or 2 and $R_1$, $R_2$, $R_3$ and $R_4$ are identical or different and are alkyl, cycloalkyl or alkenyl having not more than 8 carbon atoms, which radicals are unsubstituted or substituted by hydroxyl, alkoxy, alkylthio or cyano, or aryl or aralkyl, which are unsubstituted or substituted by hydroxyl, hydroxyalkyl, alkoxy, alkoxyalkyl, alkyl, alkylthio, cyano or halogen, or ($R_1$ and $R_2$) and/or ($R_3$ and $R_4$) together with the nitrogen atom to which they are bonded form a heterocyclic ring having 5 or 6 ring members, $M_1$, $M_2$ and $M_3$ are each acyl having 2 to 5 carbon atoms or hydrogen, $Y_1$ and $Y_2$ are identical or different from one another and have the formula $$-C_mH_{2m}- \quad (1.6)$$

in which m is an integer from 1 to 12, the sum of the m's in $Y_1$ and $Y_2$ is not less than 3 and when m is 1 the bond to the bridge member D is not made via a nitrogen atom or oxygen atom, or $Y_1$ and $Y_2$ are phenylene, which is unsubstituted or substituted by halogen, hydroxyl, al-

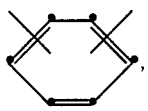 (1.19)

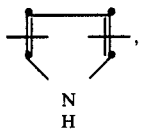 (1.20)

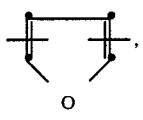 (1.21)

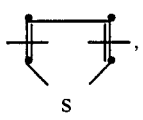 (1.22)

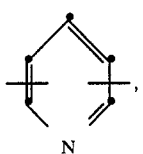 (1.23)

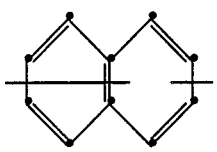 (1.24)

or

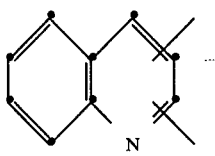 (1.25)

and the aromatic rings can be substituted by halogen, especially chlorine or bromine, alkyl or alkoxy.

Alkyl and alkoxy radicals as substituents of the aromatic bridge members of one of the formulae (1.19) to (1.25) as a rule contain 1 to 5 carbon atoms and are, for example, methyl, ethyl, propyl, isopropyl, butyl, isobutyl or tert.-butyl and also methoxy, ethoxy, propoxy, butoxy or pentoxy and the corresponding branched-chain isomers. The aromatic bridge members can contain one or several substituents.

$D_1$ is also diaminoalkylene, for example of the formula

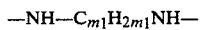 (1.26)

or in particular

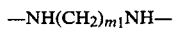 (1.27)

in which $m_1$ is an integer from 2 to 12. The alkylene groupings already mentioned are preferred.

The diaminoarylene radicals, as a further definition of $D_1$, are preferably those of the formula

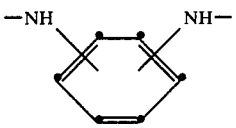 (1.28)

and in particular of the formula

 (1.29)

in which the phenyl nucleus can be substituted by halogen, especially chlorine or bromine, or alkyl or alkoxy groups, especially those having 1 to 5 carbon atoms of the type indicated above, and one or several substituents can be present on the phenyl nucleus.

The dioxy- and polyoxy-alkyleneoxy radicals which are suitable as bridge members $D_1$ can be represented by the formulae

 (1.30)

and

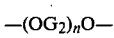 (1.31)

$G_1$ in formula (1.30) is, for example, straight-chain or branched alkylene having 2 to 12 carbon atoms; suitable groupings here are in particular again the groupings mentioned above, which can be substituted by halogen, preferably chlorine or bromine.

In formula (1.31), $G_2$ is, for example, —CH$_2$CH$_2$—,

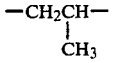

or —(CH$_2$)$_4$— and n is an integer from 2 to 15.

Examples of dioxyalkyleneoxy radicals are —O(CH$_2$)$_2$O— or —O(CH$_2$)$_4$O— and examples of polyoxyalkyleneoxy radicals are —OCH$_2$CH$_2$OCH$_2$CH$_2$O—, —(OCH$_2$OH$_2$)$_{15}$O—,

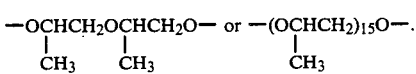

Further possible bridge members $D_1$ are dioxyarylene radicals which, for example, have the formula

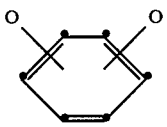 (1.32)

and in particular the formula

 (1.33)

in which the phenyl nucleus can be substituted by halogen, especially chlorine or bromine, or alkyl or alkoxy, especially those having 1 to 5 carbon atoms of the type indicated above, and one or several substituents can be present on the phenyl nucleus. A further suitable radical is that of the formula

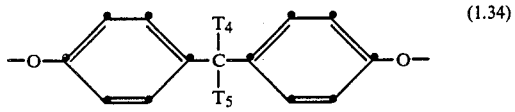
(1.34)

in which $T_4$ and $T_5$ are hydrogen or methyl.

The bridge member $D_2$ in formula (1.12) is diaminoalkylene, dioxyalkylene or polyoxyalkyleneoxy and these groupings can have the same meanings as indicated above when defining the same groupings for $D_1$. Dithioalkylene radicals $D_2$ can preferably be represented by the formula

$-SG_1S-$ (1.35)

in which $G_1$ is as defined.

$D_3$ in formula (1.13) is arylene and can in particular be phenylene, in which the phenyl ring can contain halogen or lower alkyl, for example having 1 to 4 carbon atoms, as substituents.

$D_4$ in formula (1.14) is alkylene, in particular straight-chain alkylene having 1 to 12 and preferably 2 to 6 carbon atoms. Arylene $D_4$ is in particular as defined for $D_3$.

$M_1$, $M_2$ and $M_3$ in formulae (1.1) to (1.5) are, for example, methylethylacetyl, isobutyryl, butyryl, isopropionyl or propionyl, preferably acetyl and in particular hydrogen. $T_1$, $T_2$ and $T_3$ in formulae (1.1) to (1.4) are methyl or preferably hydrogen.

As a rule, $X_1$ and $X_2$ and/or $X_3$ and $X_4$ in formula (1.1) are a direct bond if $A_1$ and/or $A_2$ are a heterocyclic ring, and are $-OOC-$ or $-COO-$ or $-O-$ if $A_1$ and/or $A_2$ are alkylene, cycloalkylene, cycloalkenylene, arylene or aralkylene, the carbon atoms in the bridge members $-OOC-$ and $-COO-$ in general being in the position adjacent to the bridge members $-A_1-$ or $-A_2-$.

Preferably, $M_1$, $M_2$ and $M_3$ in formula (1.1) and $M_1$ and $M_2$ in formulae (1.2) to (1.5) on the one hand, and $T_1$, $T_2$ and $T_3$, and also $A_1$ and $A_2$, and $X_1$ and $X_2$, and $X_3$ and $X_4$ in formula (1.1) and $T_1$ and $T_2$ in formulae (1.2) to (1.4) on the other hand, have the same meanings in each case.

Examples of heterocyclic rings having 5 or 5 ring members and 2 nitrogen atoms, as a definition of the divalent radicals $A_1$ and $A_2$ in formula (1.1), are imidazole, imidazolidine, imidazoline, piperazine, pyrazine, pyrazole, pyrazolidine, pyrazoline, pyridazine and pyrimidine rings. Furthermore, in a preferred embodiment of these heterocyclic rings, alloxane, malonylurea, which is also termed barbituric acid, oxalyl-, ethylene- and propylene-urea, uracil, dihydrouracil, diketo-2,5-pyrazine, pyrazalone or hydantoin are also suitable, 5,6-dihydrouracil and in particular 1,3-pyropylene- and ethylene-urea and hydantoin being preferred.

Suitable alkyl substituents of the heterocyclic rings are, in particular, those having 1 to 4 carbon atoms, preferably isopropyl and ethyl and in particular methyl. Examples of alkyl-substituted heterocyclic rings are thus 1-, 2-, 4- or 5-methylimidazole, 1,1-, 1,4- and 1,5-dimethylimidazole, 3- or 5-pyrazole, 3,5-dimethyl-pyrazole, 2,4-dimethylpyrimidine, 1-methylpyrazolone and 5-methyluracil, which is also termed thymine, and preferably 5,5-dimethyl-6-ethyl-5,6-dihydrouracil, 5,5,6-trimethyl-5,6-dihydrouracil and in particular 5,5-dimethyl-5,6-dihydrouracil, 6-methyl-5,6-dihydrouracil, 5-isopropyl-5-methylhydantoin, 5-ethyl-5-methylhydantoin, 5,5-dimethylhydantoin and 5-methylhydrantoin.

If the bridge members $A_1$ and $A_2$ are alkylene, suitable alkylene bridges are in particular those which have not more than 34, preferably 2 to 34 and in particular 2 to 8 carbon atoms and can be interrupted by heteroatoms, preferably oxygen atoms and in particular 1 or 2 oxygen atoms. If $X_1$ and $X_2$, and $X_3$ and $X_4$, are $-OOC-$ or $-COO-$, $A_1$ and $A_2$ are derived, for example, from acyclic aliphatic dicarboxylic acids, such as succinic acid, glutaric acid, adipic acid, pimelic acid, suberic acid, azelaic acid and sebacic acid, or also from dimerised linoleic acid.

If $X_1$ and $X_2$, and $X_3$ and $X_4$, are $-O-$, on the other hand, $A_1$ and $A_2$ are derived, for example, from acyclic aliphatic alcohols such as ethylene glycol and diethylene glycol, such as propane-1,2-diol, propane-1,3-diol, butane-1,4-diol and pentane-1,5-diol.

$A_1$ and $A_2$ are furthermore divalent bridge members in ring form, such as cycloalkylene, cycloalkenylene, arylene or aralkylene, which preferably have 5 to 26 carbon atoms, and these bridge members in ring form have 1 or 2 rings, each of which preferably has 6 ring carbon atoms and can be substituted by alkyl, preferably having 1 to 4 carbon atoms, especially by methyl or ethyl, and can be substituted by halogen, preferably bromine or chlorine. In the case of the bridge members in ring form which have two rings, these rings are bonded to one another, preferably direct, via a heteroatom, in particular the sulfone group, or via an alkylene bridge of the type indicated above, which can be interrupted by hetero-atoms, preferably 1 or 2 oxygen atoms.

Cycloalkenylene, as a bridge member, preferably is unsubstituted or substituted only by alkyl of the type described above and preferably has only one ring. Accordingly, cycloalkylene bridge members contain a total of preferably 5 to 10 carbon atoms. Cycloalkylene is likewise preferably substituted only by alkyl, but as a bridge member has either 1 or 2 rings, the two rings being bonded to one another as described above. Accordingly, cycloalkylene bridge members contain, in total, preferably 6 to 18 carbon atoms.

Arylene and aralkylene are preferably substituted only by halogen and have one ring or two rings, the two rings being bonded as described above. Alkylene radicals in aralkylene are in particular alkylene radicals having 1 to 4 carbon atoms, preferably ethylene and in particular methylene. Accordingly, arylene bridge members preferably contain a total of 6 to 18 carbon atoms and aralkylene bridge members preferably contain a total of 8 to 26 carbon atoms.

If $X_1$ and $X_2$, and $X_3$ and $X_4$, are $-OOC-$ or $-COO-$, $A_1$ and $A_2$ are derived, for example, from cycloaliphatic dicarboxylic acids such as tetrahydrophthalic acid, 4-methyltetrahydrophthalic acid, hexahydrophthalic acid and 4-methylhexahydrophthalic acid, and from aromatic dicarboxylic acids, such as phthalic acid, isophthalic acid and terephthalic acid.

If $X_1$ and $X_2$, and $X_3$ and $X_4$, are $-O-$, on the other hand, $A_1$ and $A_2$ are derived, for example, from cycloaliphatic alcohols such as resorcitol, quinitol, bis-(4- hydroxycyclohexyl)-methane, 2,2-bis-(4-hydroxycyclohexyl)-propane, and 1,1-bis-(hydroxymethyl)-cyclohex-3-ene, from aromatic alcohols, such as p,p'-bis-(2-hydroxyethylamino)diphenylmethane, from mononuclear phenols, such as resorcinol and hydroquinone, and in particular from polynuclear phenols, such as bis-(4-hydroxyphenyl)-methane, which is also termed bisphenol F, 4,4'-dihydroxydiphenyl, bis-(4-hydroxyphenyl)-sulfone, 2,2-bis-(4-hydroxyphenyl)-propane, which is also termed bisphenol A, and 2,2-bis(3,5-dibromo-4-hydroxyphenyl)-propane.

In a further embodiment $X_1$ and $X_2$ and/or $X_3$ and $X_4$ can differ from one another. Thus, for example, $X_1$ can be —O— and $X_2$ —COO—, and in this case $A_1$ is derived from salicyclic acid. Preferably, however, as already indicated, $X_1$, $X_2$, $X_3$ and $X_4$ in each case have the same meanings and as a rule are a direct bond if $A_1$ and $A_2$ are each a heterocyclic ring of the indicated type, and are —O— or —OOC— or —COO— if $A_1$ and $A_2$ are alkylene, cycloalkylene, cycloalkenylene, arylene or aralkylene.

t in formula (1.1) is 1 to 4 and preferably 1 to 3 and can be not only an integer but also can have any desired values between the integers.

The central member of the bridge members of the formula (1.2) in which v is 2 is derived from a dicarboxylic acid which, depending on the value of u, has 1 to 8 carbon atoms, such as malonic acid, succinic acid, glutaric acid, adipic acid, pimelic acid, suberic acid, azelaic acid or sebacic acid, malonic acid, succinic acid and in particular adipic acid being preferred. If, on the other hand, v in formula (1.2) is 1, the central member of these bridge members is derived from the corresponding diols, such as ethylene glycol, propane-1,3-diol, butane-1,4-diol or pentane-1,6-diol.

Preferred ammonium salts are those containing cationic units of the formula (1) in which E has the formula (1.1), i.e. ammonium salts in which the cationic units have the formula

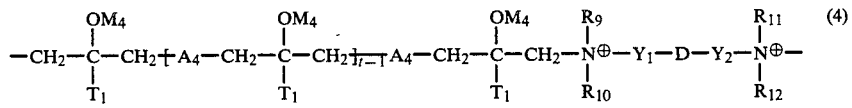

in which $A_1$, $A_2$, D, $M_1$, $M_2$, $M_3$, $R_1$, $R_2$, $R_3$, $R_4$, $T_1$, $T_2$, $T_3$, $X_1$, $X_2$, $X_3$, $X_4$, $Y_1$, $Y_2$ and t are as defined.

Further preferred ammonium salts according to the invention contain units of the formula

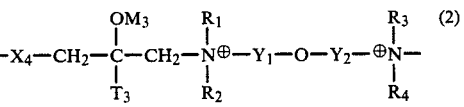

in which $R_5$, $R_6$, $R_7$ and $R_8$ are identical to or different from one another and are alkyl, hydroxyalkyl, alkoxyalkyl, alkylthioalkyl or cyanoalkyl having a total of 1 to 8 carbon atoms, cyclopentyl, cyclohexyl, alkenyl having 2 to 4 carbon atoms, unsubstituted phenyl or benzyl, or phenyl or benzyl substituted by hydroxyl, cyano, chlorine, bromine or alkyl, hydroxyalkyl, alkoxy, alkylthio or alkoxyalkyl each having 1 to 2 carbon atoms in the alkyl moiety and alkoxy moiety; or ($R_5$ and $R_6$) and ($R_7$ and $R_8$), together with the nitrogen atom to which they are bonded, form a heterocyclic ring of the formulae

or

$A_3$ is a heterocyclic ring having 5 or 6 ring members and 2 nitrogen atoms, which is unsubstituted or substituted by methyl, ethyl or isopropyl, or alkylene having 2 to 34 carbon atoms, which can be interrupted by oxygen atoms, cycloalkenylene having 6 to 10 carbons atoms, which can be substituted by methol or ethyl, or cycloalkylene which has one or two rings and has 6 to 18 carbon atoms or arylene which has one or two rings and has 6 to 18 carbon atoms or aralkylene which has one or two rings and has 8 to 26 carbon atoms, the two latter radicals being unsubstituted or substituted by bromine or chlorine, and D, $M_1$, $T_1$, $X_1$, $X_2$, $Y_1$, $Y_2$ and t are as defined, and in particular units of the formula

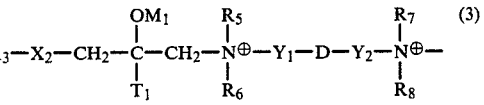

in which $R_9$, $R_{10}$, $R_{11}$ and $R_{12}$ are identical to or different from one another and are phenyl, benzyl or alkyl having 1 to 4 carbon atoms, or ($R_9$ and $R_{10}$) and ($R_{11}$ and $R_{12}$), together with the nitrogen atom to which they are bonded, form a piperidine ring, $M_4$ is propionyl, acetyl or hydrogen, $A_4$ is a divalent radical of one of the formulae

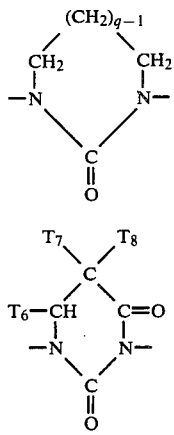

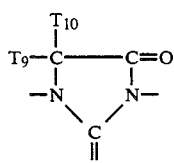

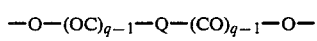

(4.1)

(4.2)

(4.3)

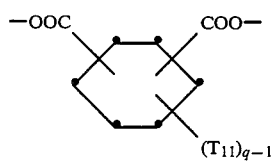

$-O-(OC)_{q-1}-Q-(CO)_{q-1}-O-$ (4.4)

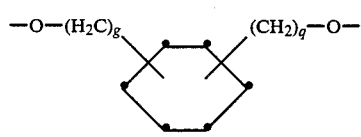

(4.5)

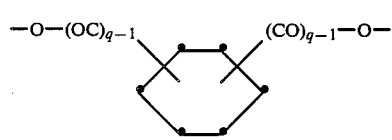

(4.6)

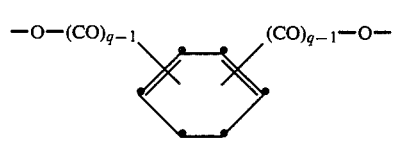

(4.7)

$-O-(CO)_{q-1}\phantom{xxxx}(CO)_{q-1}-O-$ (4.8)

-continued or

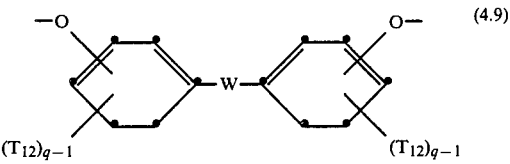

(4.9)

in which Q is alkylene having 2 to 8 carbon atoms, which can be interrupted by 1 or 2 oxygen atoms, W is a direct bond, —SO$_2$— or alkylene having 1 to 4 carbon atoms, T$_6$, T$_7$, T$_8$ and T$_9$ are each hydrogen or methyl, T$_{10}$ is hydrogen, methyl, ethyl or isopropyl, T$_{11}$ is methyl or ethyl, T$_{12}$ is chlorine or bromine and q is 1 or 2, and D, Y$_1$, Y$_2$ and t are as defined in formula (1) or (1.1), or especially units of the formula

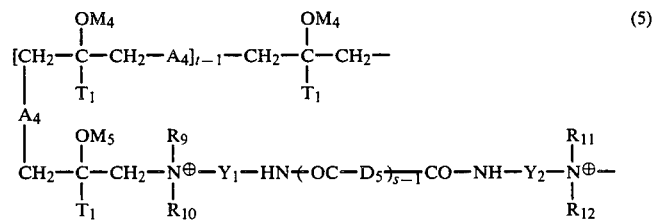

(5)

in which s is 1 or 2, D$_5$ is a direct bond or a divalent bridge member of one of the indicated formulae (1.15) to (1.31) or alkylene having 1 to 6 carbon atoms, and Y$_1$, Y$_2$ and t are as defined in formula (1.3) and A$_4$, M$_4$, R$_9$, R$_{10}$, R$_{11}$ and R$_{12}$ are as defined in formula (4).

In a particularly preferred embodiment, the ammonium salts according to the invention contain units of the formula

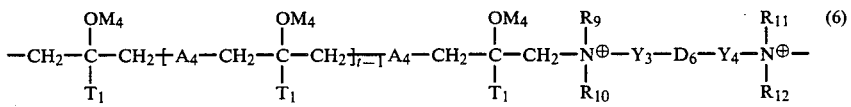

(6)

in which D$_6$ has one of the formulae

(6.1)

(6.2)

$$-\overset{O}{\underset{\|}{C}}-S-(CH_2)_{m1}-S-\overset{O}{\underset{\|}{C}}-,$$ (6.3)

$$-\overset{O}{\underset{\|}{C}}-NH-(CH_2)_{m1}-NH-\overset{O}{\underset{\|}{C}}-$$ (6.4)

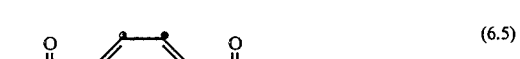

(6.5)

$$-O\overset{O}{\underset{\|}{C}}-NH-(CH_2)_{m1}-NH-\overset{O}{\underset{\|}{C}}O-,$$ (6.6)

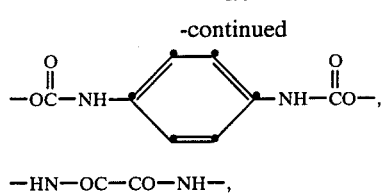 (6.7)

—HN—OC—CO—NH—,  (6.8)

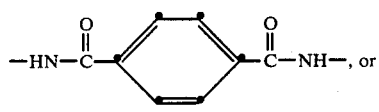 (6.9)

—HN—CO—(CH$_2$)$_{m1}$—CO—NH—  (6.10)

or one of the indicated formulae (1.7), (1.9), (1.10) or (1.11), G$_1$ in formula (6.1) and G$_2$ and n in formula (6.2) being as defined for formulae (1.30) and (1.31) and m$_1$ in the formulae (6.3), (6.4), (6.6) and (6.10) being an integer from 2 to 12, and Y$_3$ and Y$_4$ are each alkylene having 1 to 6 carbon atoms or phenylene and A$_4$, M$_4$, R$_9$, R$_{10}$, R$_{11}$ and R$_{12}$ are as defined in formula (4) and T$_1$ and t are as defined in formula (1.1).

Ammonium salts according to the invention which are of primary interest are those which contain units which in particular have the formula

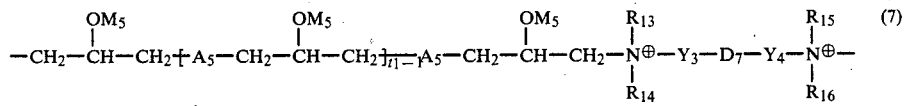 (7)

in which R$_{13}$, R$_{14}$, R$_{15}$ and R$_{16}$ are each benzyl, methyl or ethyl, or (R$_{13}$ and R$_{14}$) and (R$_{15}$ and R$_{16}$), together with the nitrogen atom to which they are bonded, form a piperidine ring, M$_5$ is acetyl or hydrogen and t$_1$ is a number from 1 to 3, A$_5$ is as defined for the indicated formulae (4.3), (4.4), (4.7) or (4.9), D$_7$ is as defined for the indicated formulae (1.7), (1.9), (6.5), (6.8), (6.9) or (6.10), M$_5$ is as defined in formula (5) and Y$_3$ and Y$_4$ are as defined in formula (6).

In another preferred embodiment, ammonium salts according to the invention contain cationic units of the formula (1) in which E has one of the formulae (1.2) to (1.5). If E has the formula (1.2), such ammonium salts contain cationic units of the formula

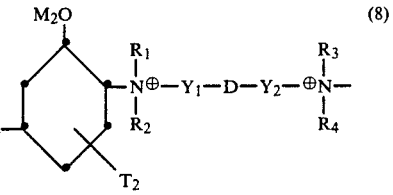 (8)

in which D, M$_1$, M$_2$, R$_1$, R$_2$, R$_3$, R$_4$, T$_1$, T$_2$, Y$_1$, Y$_2$, u and v are as defined in formula (1) or (1.2).

Preferred ammonium salts are those which contain cationic units of the formula

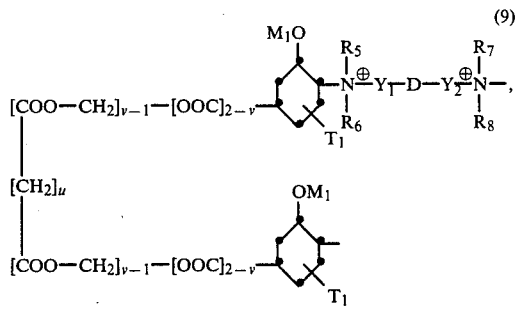 (9)

in which D, M$_1$, T$_1$, Y$_1$, Y$_2$, u and v are as defined in formula (1) or (1.2) and R$_5$, R$_6$, R$_7$ and R$_8$ are as defined in formula (3), in particular of the formula

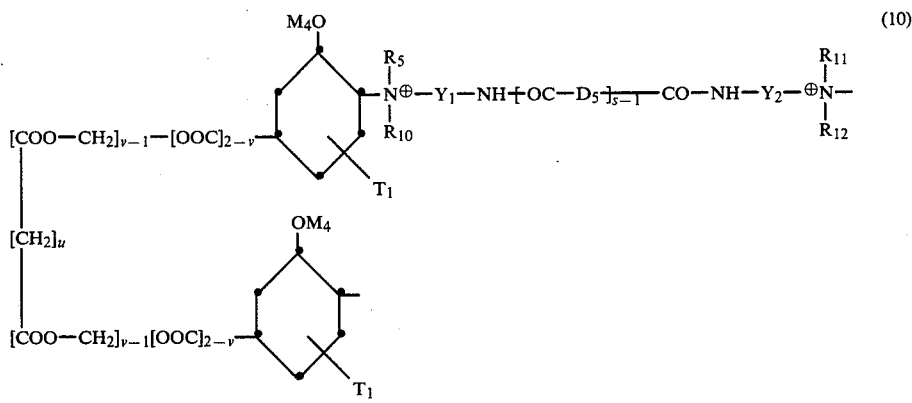 (10)

in which T$_1$, Y$_1$, Y$_2$, u and v are as defined in formula (1) or (1.2) and M$_4$, R$_9$, R$_{10}$, R$_{11}$ and R$_{12}$ are as defined in formula (4) and D$_5$ and s are as defined in formula (5), and especially of the formula

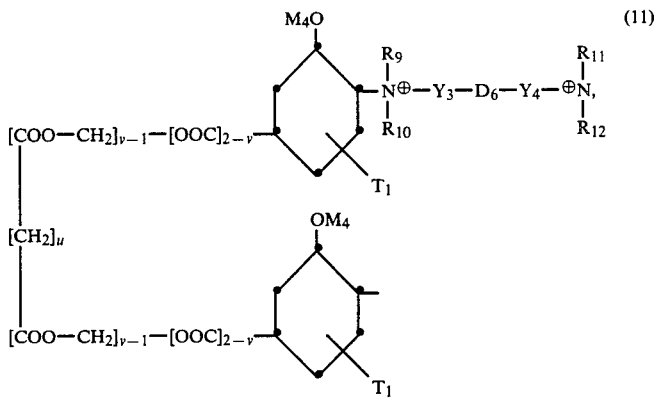

in which $T_1$, u and v are as defined in formula (1) or (1.2), $M_4$, $R_9$, $R_{10}$, $R_{11}$ and $R_{12}$ are as defined in formula (4) and $D_6$, $Y_3$ and $Y_4$ are as defined in formula (6).

If v in the formulae (1.2) and (8) to (10) is 1, the cationic units of the ammonium salts of that embodiment, which is of primary interest, have the formula

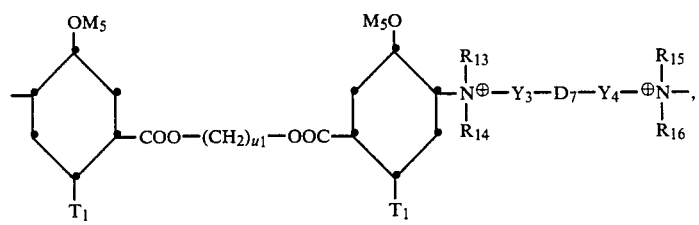

in which $u_1$ is an integer from 1 to 4 and $T_1$ is as defined in formula (1.2), $Y_3$ and $Y_4$ are as defined in formula (6) and $D_7$, $M_5$, $R_{13}$, $R_{14}$, $R_{15}$ and $R_{16}$ are as defined in formula (7).

The ammonium salts which contain cationic units of the formulae (8) to (11) in which v is 2 are preferred to the ammonium salts which contain cationic units of the formulae (8) to (10) in which v is 1. In this particularly preferred embodiment, the ammonium salts which are of primary interest contain cationic units which have the formula

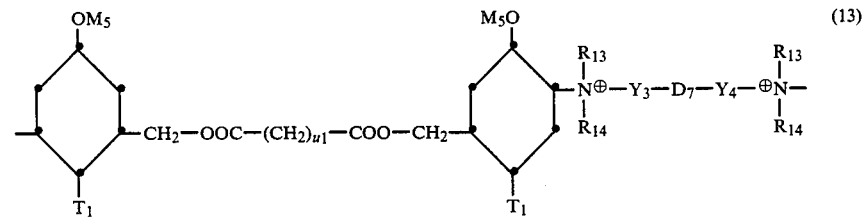

in which $u_1$ is an integer from 1 to 4, $T_1$ is as defined in formula (1.2), $Y_3$ and $Y_4$ are as defined in formula (6) and $M_5$, $D_7$, $R_{13}$, $R_{14}$, $R_{15}$ and $R_{16}$ are as defined in formula (7).

In a further embodiment of the ammonium salts according to the invention which contain cationic units of the formula (1) in which E has the formula (1.3), (1.4) or (1.5), preferred ammonium salts are those which contain cationic units which have one of the formulae

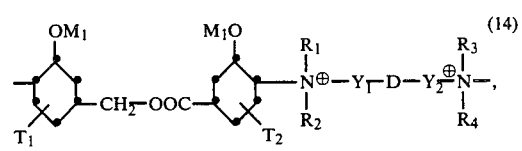

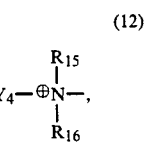

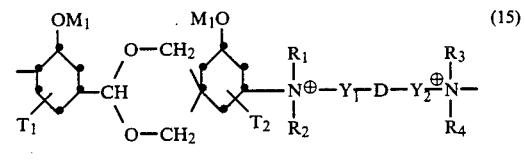

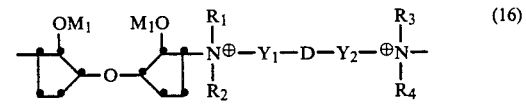

in which D, $M_1$, $R_1$, $R_2$, $R_3$, $R_4$, $T_1$, $Y_1$ and $Y_2$ are as defined in formula (1) or (1.3) to (1.5).

Further preferred ammonium salts are those which contain cationic units of one of the formulae

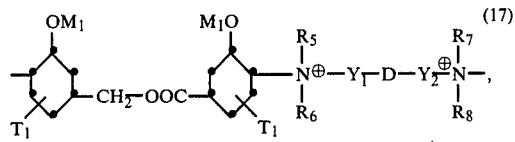 (17)

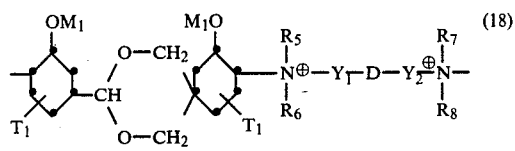 (18)

or

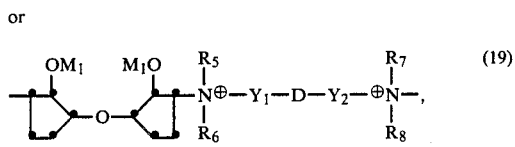 (19)

in which D, $M_1$, $T_1$, $Y_1$ and $Y_2$ are as defined in formula (1) or (1.3) to (1.5) and $R_5$, $R_6$, $R_7$ and $R_8$ are as defined in formula (3), in particular of one of the formulae

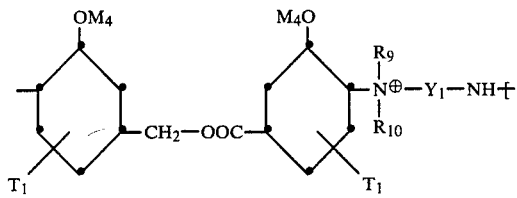 (20)

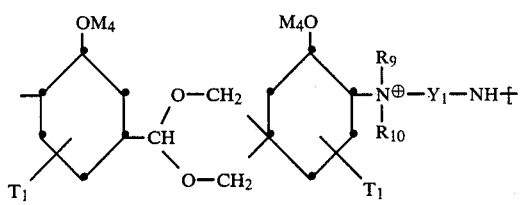 (21)

or

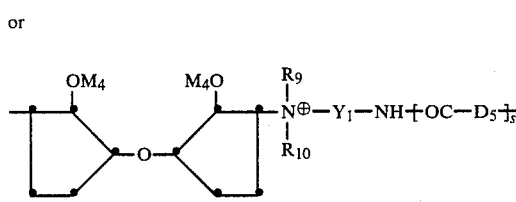 (22)

in which $T_1$, $Y_1$ and $Y_2$ are as defined in formula (1) or (1.3) to (1.5), $M_4$, $R_9$, $R_{10}$, $R_{11}$ and $R_{12}$ are as defined in formula (4) and $D_5$ and s are as defined in formula (5), and especially of one of the formulae

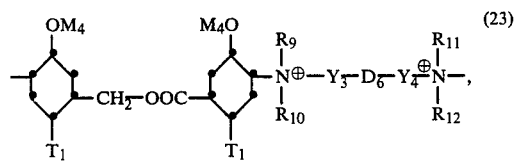 (23)

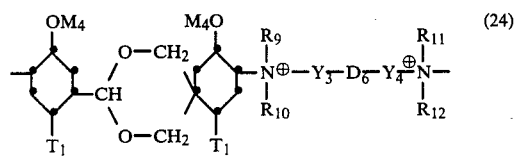 (24)

-continued or

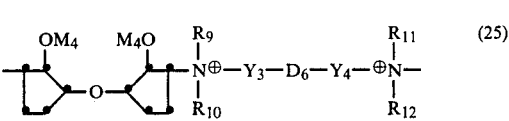 (25)

in which $T_1$ is as defined in formulae (1.3) to (1.5), $M_4$, $R_9$, $R_{10}$, $R_{11}$ and $R_{12}$ are as defined in formula (4) and $D_6$, $Y_3$ and $Y_4$ are as defined in formula (6).

The cationic units of the ammonium salts of this embodiment, which are of primary interest, have one of the formula

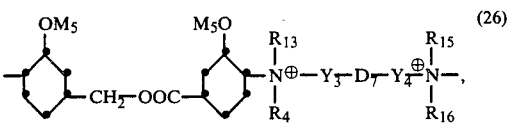 (26)

(27)

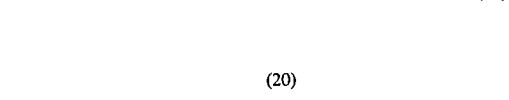

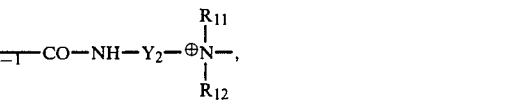 (28)

in which $Y_3$ and $Y_4$ are as defined in formula (6) and $M_5$, $D_7$, $R_{13}$, $R_{14}$, $R_{15}$ and $R_{16}$ are as defined in formula (7).

Specific representatives of the ammonium salts according to the invention contain, for example, cationic units of the formulae

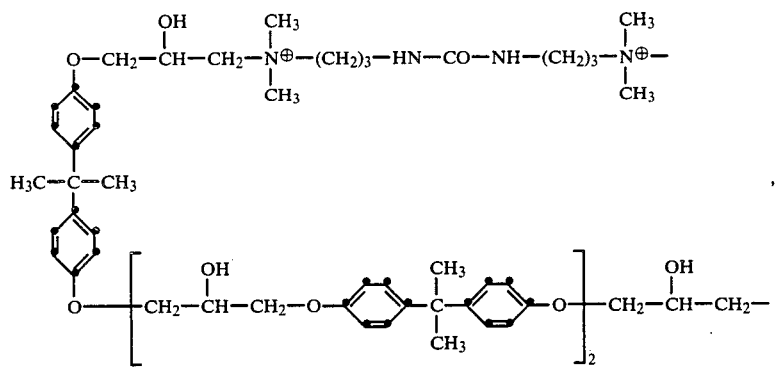
(29.1)
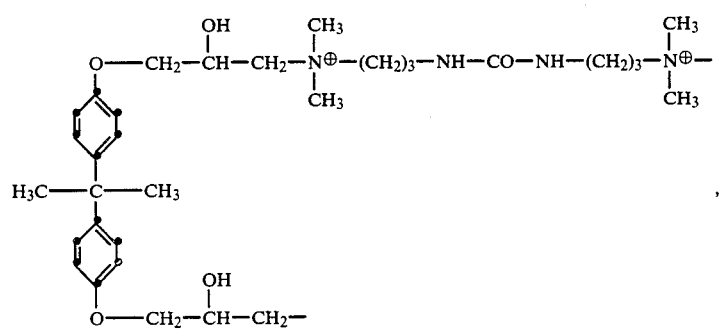
(29.2)
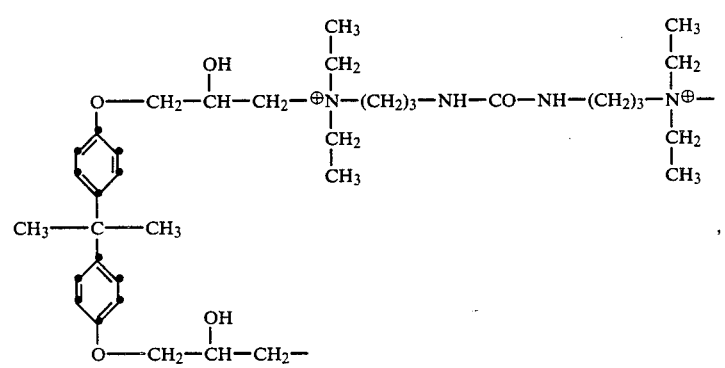
(29.3)
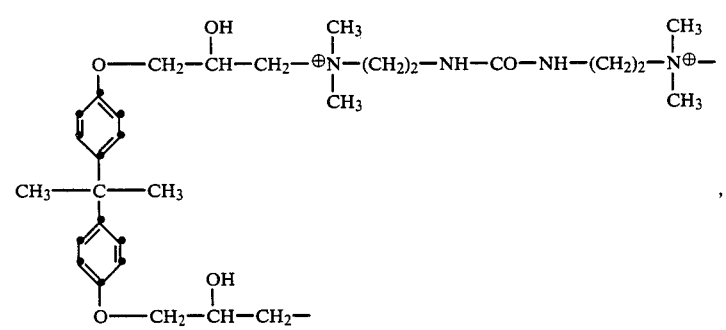
(29.4)
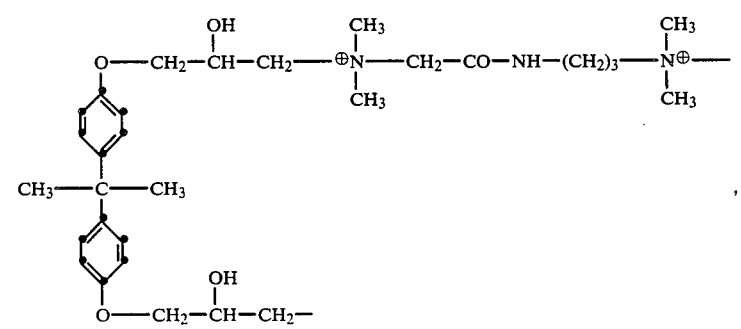
(29.5)

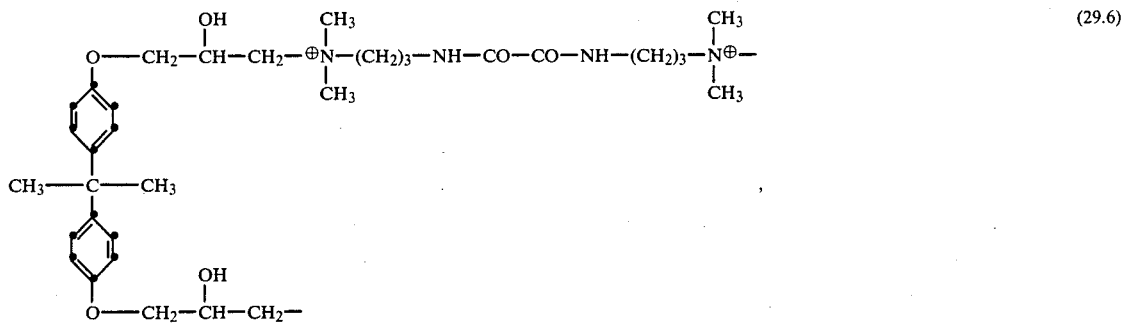
(29.6)
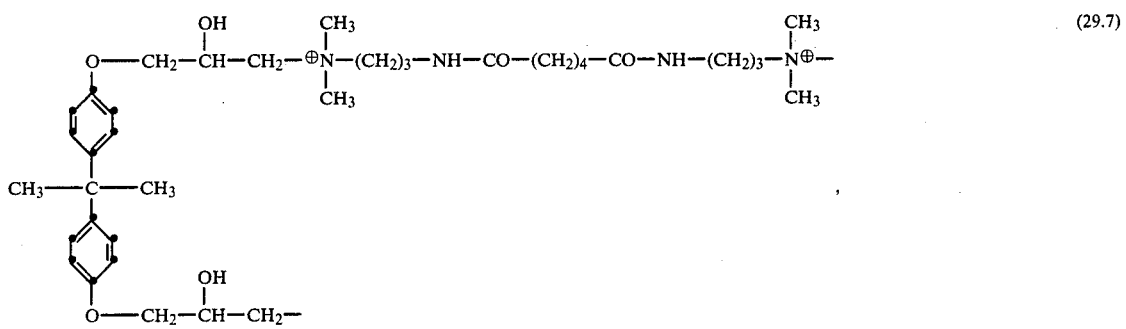
(29.7)
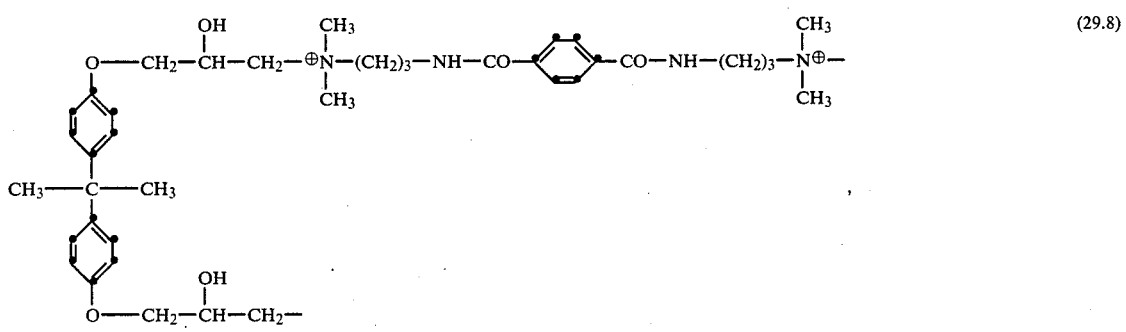
(29.8)
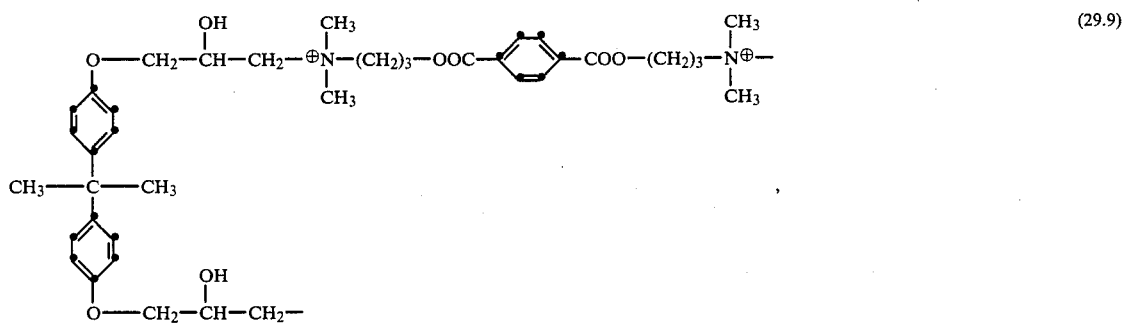
(29.9)
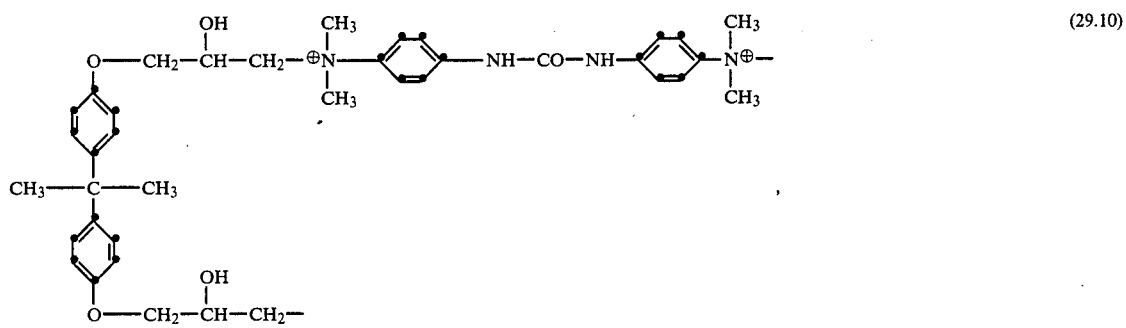
(29.10)

-continued
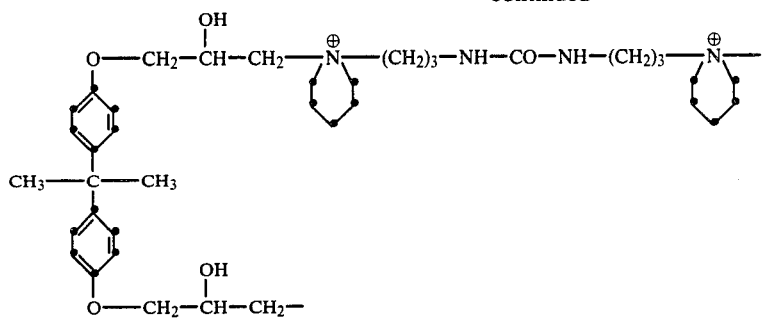 (29.11)
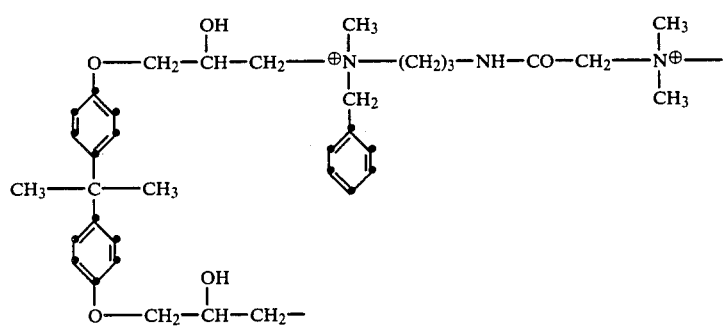 (29.12)
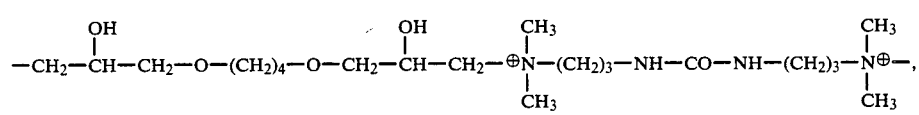 (29.13)
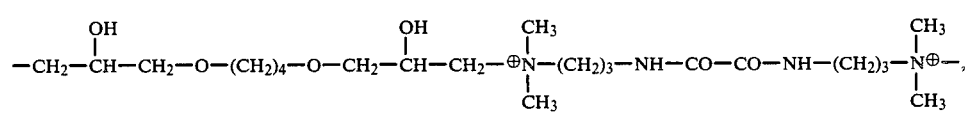 (29.14)
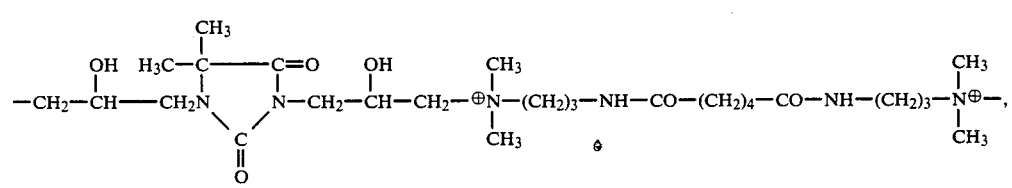 (29.15)
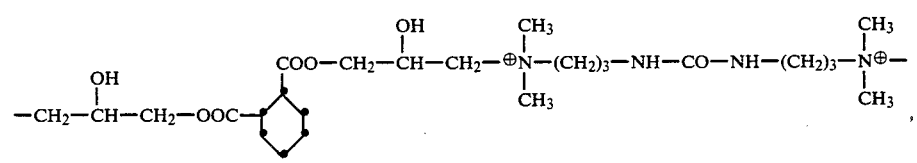 (29.16)
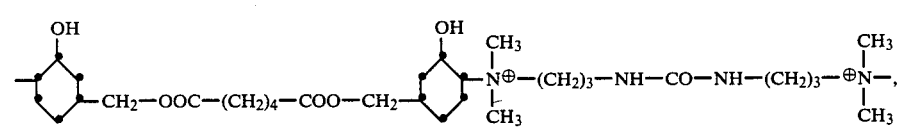 (29.17)
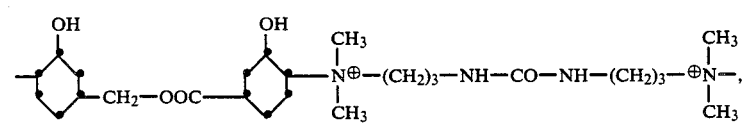 (29.18)
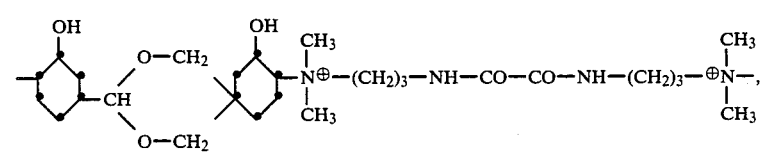 (29.19)

-continued

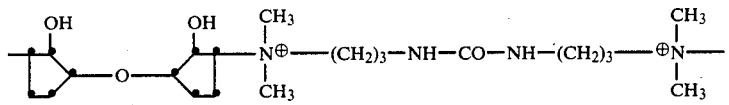
(29.20)

or

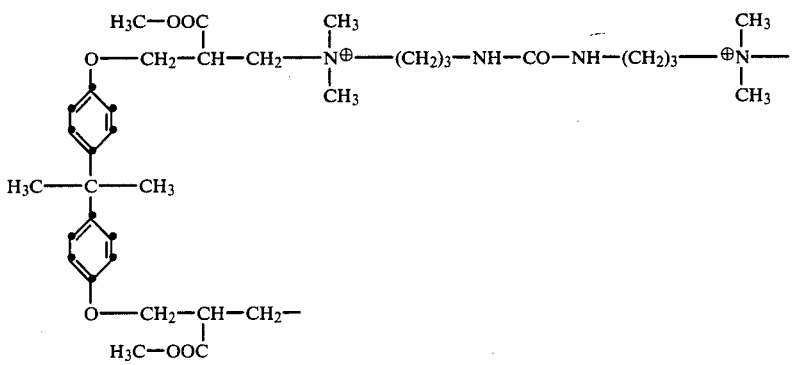
(29.21)

The average molecular weight of the ammonium salts is about 1,000 to about 120,000 and preferably about 1,000 to about 35,000. It can be seen from this that the ammonium salts comprise not only one but also in particular several recurring units of one of the indicated formulae (1) to (29), the recurring units as a rule being identical. On average, the ammonium salts contain 1 to about 100 and preferably 1 to about 30 such units.

Suitable anions for the quaternary ammonium salts are all conventional inorganic or organic anions with the proviso that the cationic units of the formula (1) do not form any complexes, with these anions, which are sparingly soluble in water, in lower alkanols or in aqueous surfactant systems.

Suitable higher-molecular organic anions are those of anionic, conventional surfactants.

Examples of such surfactant anions are: alkyl- and alkylene-carboxylates, alkyl ether-carboxylates, fatty alcohol-sulfates, fatty alcohol ether-sulfates, alkylolamide-sulfates and -sulfonates, fatty acid alkylolamide polyglycol ether-sulfates, alkylphenylglycol ether-sulfonates, sulfosuccinic acid half-esters and diesters or fatty alcohol ether-phosphates, in which the fatty radicals or alkyl radicals contain as a rule 8 to 24 and preferably 12 to 18 carbon atoms and are derived from the corresponding fatty acids, for example oleic acid, palmitic acid, stearic acid, linoleic acid and linolenic acid and also behenic acid and clupanodonic acid, in particular in the form of their industrial mixtures. Radicals of the fatty acids of the indicated type are also suitable as anions. This applies in particular in the case of the anions oleate, palmitate and especially laurate and stearate.

Anions of low-molecular organic acids, for example of organic acids having 1 to 4 carbon atoms, such as formic acid, acetic acid, propionic acid and oxalic acid, of aromatic sulfonic acids having 6 to 9 carbon atoms, such as benzene- and toluene-sulfonic acid, and in particular of mineral acids or of their alkyl esters having 1 to 4 carbon atoms in the alkyl radical, such as a hydrogen halide acid, nitric acid, sulfuric acid and alkyl sulfates, are, however, preferred. Suitable anions are, for example, the halogen anions, such as $I^{\ominus}$, $Br^{\ominus}$ and especially $Cl^{\ominus}$, methyl-sulfate ($CH_3SO_4^{\ominus}$), ethyl-sulfate ($C_2H_5SO_4^{\ominus}$), toluenesulfonate, acetate, nitrate and sulfate. Stearate, ethyl-sulfate and sulfate, in particular laurate, methyl-sulfate and bromide and especially chloride are of primary interest. Ammonium salts containing surfactant anions or anions of fatty acids of the indicated type are, for example, soluble in methanol, ethanol and isopropanol and in mixtures thereof with water and also in aqueous surfactant systems. Ammonium salts containing anions of mineral acids or of low-molecular organic acids of the indicated type are water-soluble.

The ammonium salts can be prepared by known methods, by, for example, reacting either diamine salts with corresponding diepoxides or diepoxide mixtures or diamines with corresponding dihalogenohydrins or dihalogenohydrin mixtures, which have been preformed by hydrolysis of the said diepoxides or diepoxide mixtures with a hydrogen halide, in molar ratios of about 1:2 to 2:1 and preferably of 1:0.9 to 1:1.1 and in particular in equimolar amounts, and, if desired, further reacting the resulting reaction products or reaction product mixtures with an acid anhydride, or mixture of acid anhydrides, in the said molar ratios to give the corresponding esters or ester mixtures.

Thus, the compounds containing units of the formula (1) can be prepared by reacting a diepoxide or a diepoxide mixture of one of the formulae

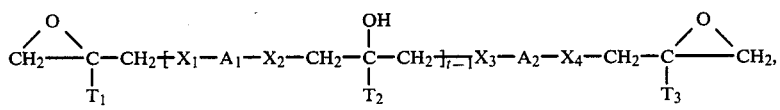
(30.1)

-continued

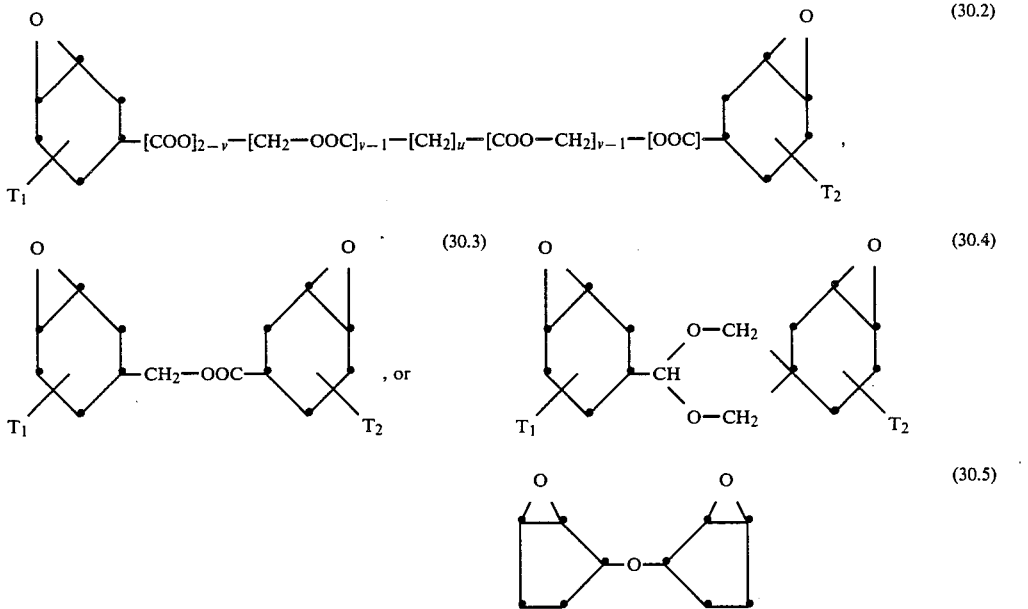

with a di-tertiary amine salt of the formula

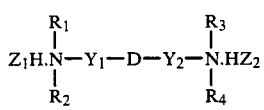  (31)

or by converting a diepoxide or diepoxide mixture of one of the formulae (30.1) to (30.5) to a dihalogenohydrin or dihalogenohydrin mixture of one of the formulae and then receiving the said dihalogenohydrin or dihalogenohydrin mixture with a di-tertiary amine of the formula

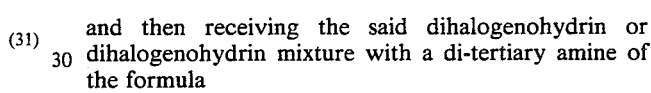  (34)

$Z_3H$  (32)

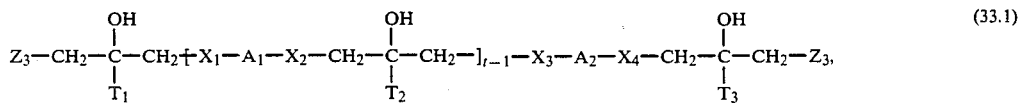

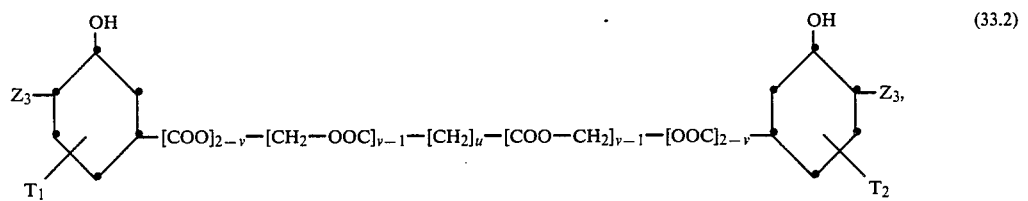

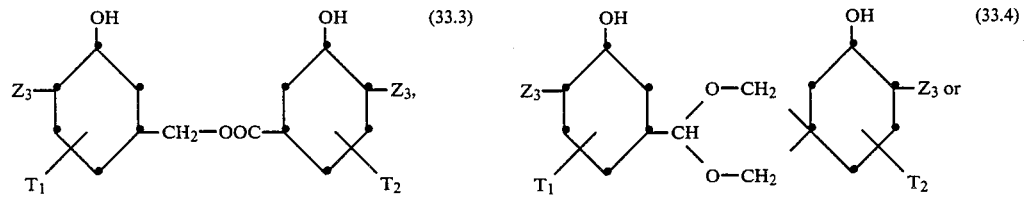

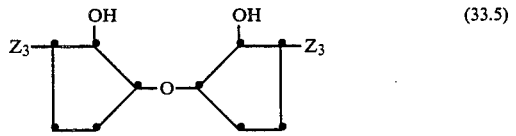

using a hydrogen halide of the formula and, if desired, further reacting the resulting reaction products or reaction product mixtures of (30.1) to (30.5)

and (31) or of (33.1) to (33.5) and (34), which contain units of one of the formulae
(36.2)
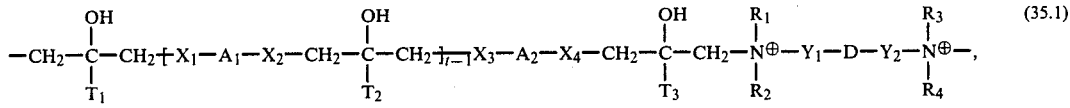
(35.1)
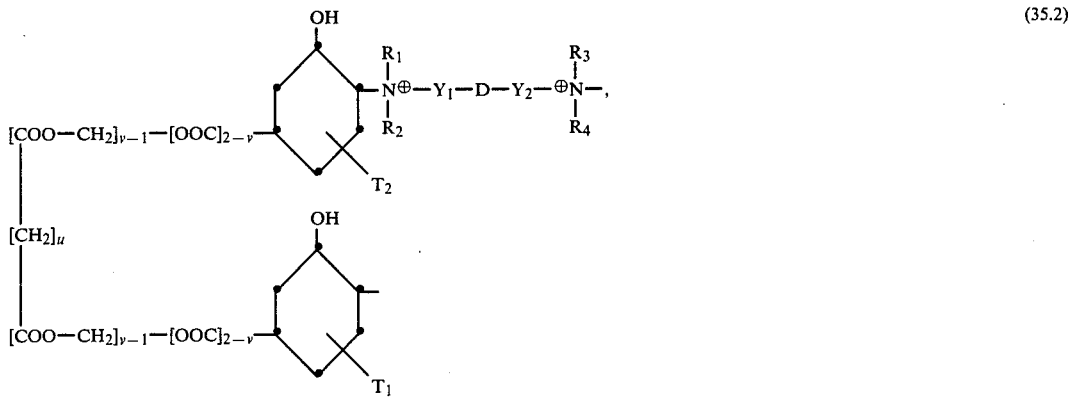
(35.2)
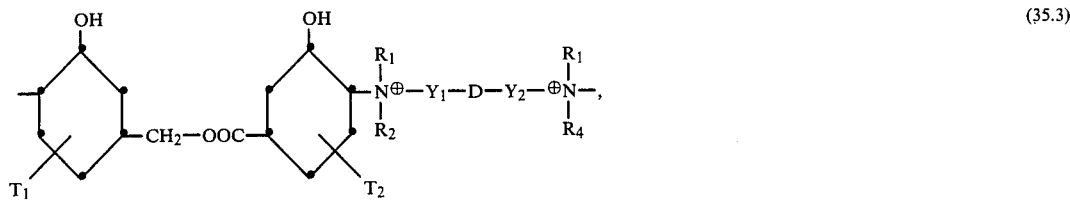
(35.3)
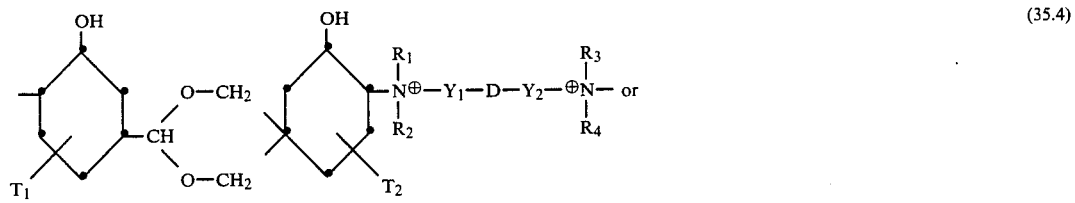
(35.4)
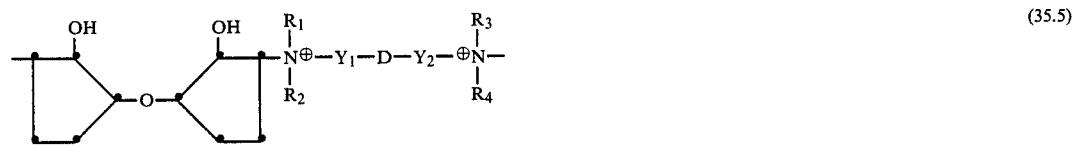
(35.5)
with an acid anhydride or mixture of acid anhydrides of the formulae
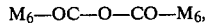
(36.1)
and/or
(36.3)
to give the corresponding esters, which contain units of one of the formulae
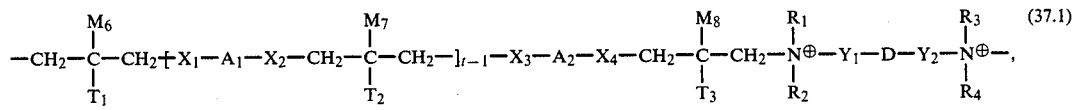
(37.1)

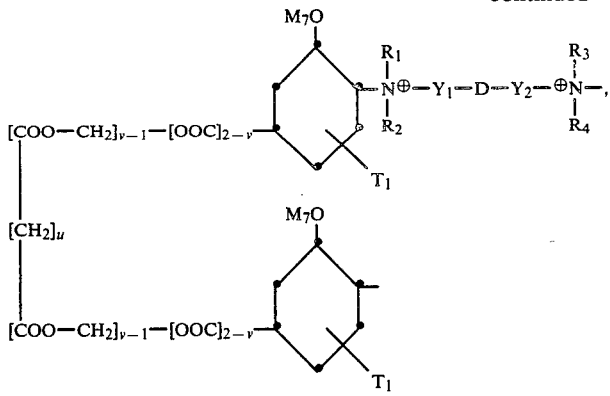
(37.2)

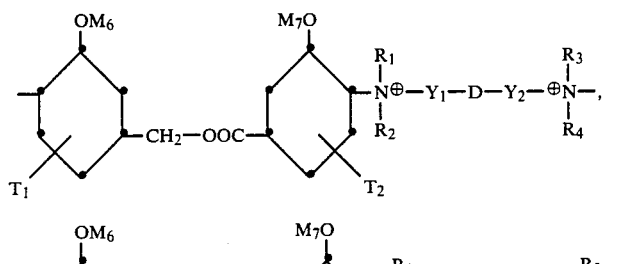
(37.3)

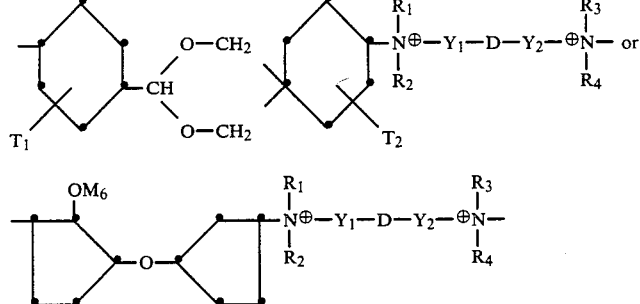
(37.4)

(35.5)

in which formulae $Z_1$ and $Z_2$ are each a surfactant anion, a fatty acid anion, an anion of low-molecular acids or mineral acids of the abovementioned type or preferably halogen, $Z_3$ is halogen and $M_6$, $M_7$ and $M_8$ are each acyl having 2 to 3 carbon atoms and $A_1$, $A_2$, D, $R_1$, $R_2$, $R_3$, $R_4$, $T_1$, $T_2$, $T_3$, $X_1$, $X_2$, $X_3$, $X_4$, $Y_1$, $Y_2$, t, u and v are as defined in formula (1).

Chlorine is of primary interest as halogen for $Z_1$, $Z_2$ and $Z_3$ in the formulae (31), (32) and (33.1) to (33.5).

An epoxide or epoxide mixture which has either the formula (30.1) or the formula (30.2), or (30.3), (30.4) and (30.5), is used as the starting material for the preparation of the ammonium salts according to the invention. Thus, mixtures of compounds of the formula (30.1) with compounds of the formulae (30.2), or (30.3), (30.4) and (30.5) are not suitable as epoxide mixtures. Correspondingly, possible end products are only reaction products or reaction product mixtures which contain units of one of the formula (35.1) to (35.5) or (37.1) to (37.5) and not mixtures of units of the formula (35.1) with, for example, (35.2) to (35.5), or (37.1) with, for example, (37.2) to (37.5).

To obtain the products or product mixtures which contain units of one of the formulae (35.1) to (35.5), the single-stage reaction of the compounds of one of the formulae (30.1) to (30.5) with the compounds of the formula (31) is preferred to the two-stage reaction of the compounds of one of the formulae (30.1) to (30.5) with the compound of the formula (32) to give compounds of one of the formulae (33.1) to (33.5), which subsequently are reacted with the compounds of the formula (34). The reaction of the products which contain units of one of the formulae (35.1) to (35.5) with the compounds of the formulae (36.1), (36.2) and/or (36.3) is optional and is carried out only if $M_1$, $M_2$ and/or $M_3$ in formulae (1.1) to (1.5) are acyl.

In a preferred embodiment of the process of preparation according to the invention, the diepoxide or diepoxide mixture of the formula (30.1) is reacted with the diamine of the formula (31), in which $Z_1$ and $Z_2$ are each halogen, or a diepoxide or diepoxide mixture of the formula (30.1) is converted to a dihalogenohydrin or dihalogenohydrin mixture of the formula (33.1) using the hydrogen halide of the formula (32) and the said dihalogenohydrin or dihalogenohydrin mixture is then reacted with a di-tertiary amine of the formula (34), the resulting reaction products or reaction product mixtures of (30.1) and (31) or of (33.1) and (34), which contain units of the formula (35.1), being further reacted, if desired, with an acid anhydride or mixture of acid anhydrides of the formulae (36.1), (36.2) and/or (36.3) to give the corresponding esters, which contain units of the formula (37.1).

The starting compounds (diamines and diepoxides) for the preparation of the quaternary ammonium salts according to the invention are in general known compounds which are easily accessible by chemical synthesis.

With the preferred single-stage or two-stage reaction of the compounds of one of the formulae (30.1) to (30.5) with the compounds of the formula (31) and, if desired, (36.1) to (36.3), ammonium salts containing cationic units of the formula (1) or of one of the formulae (35.1) to (35.5) or (37.1) to (37.5) are obtained which contain surfactant anions, fatty acid anions, anions of low-molecular acids of the abovementioned type or halogen anions as the ion of opposite charge, whilst with the two-stage or three-stage reaction of the compounds of one of the formulae (30.1) to (30.5) with the compounds of the formulae (32) and (34) and, if desired, the compounds of the formulae (36.1) to (36.3), ammonium salts containing cationic units of the formula (1) or of one of the formulae (35.1) to (35.5) or (37.1) to (37.5) are obtained which, on the other hand, contain only halogen ions as the ion of opposite charge.

Diamines with the urea bridge member (—HNCONH—) and an alkylene bridge member to the tertiary nitrogen atoms can be obtained by reacting urea with alkylenediamines, which contain a tertiary nitrogen atom, at elevated temperatures with the elimination of ammonia. Another possibility for the preparation of the diamines comprises the reaction of the corresponding α,ω-dihalogeno compounds with secondary amines. The diamines with a bridge member which is derived from dicarboxylic acids can be prepared, for example, for the dichlorides or dialkyl esters of the acids and alkylenediamines.

Diepoxides which have two terminal 1,2-epoxide groups bonded to aliphatic chains contain, depending on the meaning of $T_1$, $T_2$ and $T_3$, groups of the formula

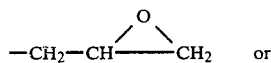 (30.6)

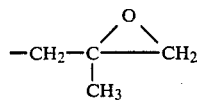 (30.7)

which are bonded to the oxygen atoms of the bridge members —COO—, —OOC— and —O—, which are present as $X_1$ and $X_2$ and/or as $X_3$ and $X_4$, or to the nitrogen atom of the bridge member $A_1$ and/or $A_2$, if $A_1$ and/or $A_2$ are a heterocyclic ring containing 2 nitrogen atoms and $X_1$ and $X_2$ and/or $X_3$ and $X_4$ are a direct bond. Thus, depending on the meaning of $X_1$ and $X_2$ and of $X_3$ and $X_4$ and also of $A_1$ and $A_2$, the diepoxides are O,O'-diglycidyl esters or ethers or di-(β-methylglycidyl)esters or ethers of aliphatic, cycloaliphatic or aromatic compounds containing two carboxylic acid groups per molecule or two alcoholic or phenolic hydroxyl groups per molecule, or are N,N'-diglycidyl compounds of heterocyclic compounds containing two nitrogen atoms per molecule. These diglycidyl compounds can be obtained by reacting the corresponding compounds containing carboxylic acid groups, hydroxyl groups or nitrogen atoms with an epihalogenohydrin or a β-methylhalogenohydrin in the presence of alkali or also in the presence of an acid catalyst with subsequent treatment with alkali and, as mentioned initially, are particularly readily accessible.

Cycloaliphatic diepoxides contain groups of the formulae

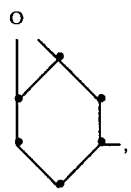 (30.8)

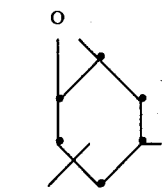 (30.9)

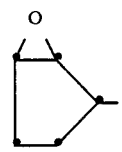 (30.10)

The diepoxides containing groups of the formula (30.8) or (30.9) can be obtained by epoxidation of the double bond of corresponding tetrahydrobenzene derivatives with, for example, peracetic acid or preferably hypochlorous acid, or chlorine in an alkaline medium, the tetrahydrobenzene derivatives being readily obtainable as intermediates from butadiene and aldehydes such as crotonaldehyde or acrolein and being subjected to a condensation reaction with one another, esterified or further reacted with dicarboxylic acids or diols, The diepoxide containing groups of the formula (30.10) can be obtained by epoxidation of the double bonds, in the manner described above, of a dicyclopentenyl ether, this ether being readily obtainable from cyclopentadiene. Thus, the cycloaliphatic diepoxides of the indicated type are also particularly readily accessible as products produced in a large scale in the plastics industry for the preparation of epoxide resins.

The ammonium salts according to the invention are prepared by reacting the compounds of the formulae (30.1) to (30.5) and (31) or (33.1) to (33.5) and (34) and, if desired, the compounds of the formulae (36.1) to (36.3) at about 20° to 150° C. As a rule, the reactions are carried out, for example, in the melt or preferably in solvents which are inert towards the reactants, for example in alcohols, glycols, ketones, such as acetone, or cyclic ethers, such as dioxane or tetrahydrofuran. Preferred alcohols are the lower alcohols, in particular methanol and especially isopropanol and ethanol. Polar solvents such as ether-alcohols, especially 1-methoxy-2-ethanol, are also preferred. The indicated reaction temperatures usually depend on the boiling points of the solvents used.

If desired, the reactions can also be carried out in water or water/alcohol mixtures as solvents.

In the case of the optional further reaction of the reaction products or reaction product mixtures, which contain units of one of the formulae (35.1) to (35.5), with the acid anhydride or mixture of acid anhydrides of the formulae (36.1) to (36.3) it is advantageous to use an esterification catalyst, for example a substituted or unsubstituted pyridine, preferably 4-dialkylaminopyridines and in particular 4-dimethylaminopyridine.

As a result of the preferred use of inexpensive and readily accessible dichloro compounds, i.e. of compounds of the formulae (31) or (33.1) to (33.4), in which $Z_1$, $Z_2$ and $Z_3$ are chlorine, for the preparation of the quaternary ammonium salts according to the invention, the salts preferentially contain chlorine ions as the anions. The introduction of other anions can preferably be carried out by introducing other anions, for example surfactant ions, into the ammonium salts containing the chlorine ions (the reaction products) by ion exchange. However, in a further embodiment of the process of preparation it is also possible to use ditertiary amine salts of the formula (31) which already contain anions other than halogen anions, i.e. surfactant anions, fatty acid anions or anions of low-molecular acids of the abovementioned type, as starting materials.

The quaternary ammonium salts which contain units of the formula (1) have, inter alia, interesting cosmetic properties if they are included in cosmetics which are used as such and are applied, for example, to the skin or preferably to the hair, and the present invention also relates to cosmetics which contain ammonium salts containing the units of the formula (1) and to processes for the preparation of the cosmetics and for the treatment of hair, especially human hair, and the hair, especially wigs, treated according to the process. These cosmetics in general additionally contain at least one conventional assistant used in cosmetics.

The cosmetics according to the invention can contain the ammonium salts containing units of the formula (1) either as the active main constituent or as an additive.

These cosmetics can be in the form of aqueous, alcoholic or aqueous-alcoholic solutions, the alcohol used being lower alcohols such as ethanol or isopropanol, or in the form of emulsions or also in the form of creams, gels or powders or in tablet form and also in the form of aerosols, which additionally contain a propellant.

In addition, the cosmetics according to the invention can contain further additives customary in cosmetics, for example preservatives, aroma substances, dyes, solvents, opacifying agents and agents imparting a pearly sheen, for example esters of fatty acids with polyols or dispersions based on copolymers; thickeners, and also vegetable extracts, protein derivatives, such as gelatin, collagen hydrolysis products, polypeptides on a natural and synthetic basis, lecithin, lanolin and lanolin derivatives, fats, oils, fatty alcohols, silicones, deodorising agents, substances which have an antimicrobial action and sequestering agents.

The cosmetics according to the invention can be either in the form of ready-for-use compositions or in the form of concentrates, which have to be diluted before use.

The cosmetics for the skin are, for example, in the form of creams, gels, emulsions or aqueous, alcoholic or aqueous-alcoholic solutions.

The further additives contained in these cosmetics are, for example, perfumes, dyes, preservatives, sequestering agents, emulsifiers and thickeners.

These compositions for the skin are, for example, skin-care creams or lotions for the hands or the face, sun-ray filter creams, tinted creams, foaming oils or liquids for the bath or deodorant preparations.

These compositions are prepared by the conventional methods, by mixing the components of the composition.

For example, in order to obtain a cream, a liquid phase, whoch contains polymers and, if desired, other additives, and an oily phase can be emulsified.

The oily phase can consist of diverse products, for example paraffin oil, petroleum jelly oil, olive oil or fatty acid esters, such as glycerol monostearate, ethyl palmitate or isopropyl palmitate or alkyl myristates, such as propyl myristate, butyl myristate or cetyl myristate. In addition, fatty alcohols, such as cetyl alcohol, or waxes, for example beeswax, can be added.

The quaternary ammonium salts according to the invention can be present, in the cosmetics for the skin, either as an additive or as the active main constituent in skin-care creams or lotions for the hands or the face, or as an additive in sun-ray filter creams, tinted creams, make-up remover milk or foaming liquids for the bath.

The cosmetics for treatment of the hair are of primary interest.

In general, the concentration of the quaternary ammonium salts, which contain units of the formula (1), in the hair cosmetics according to the invention is 0.01 to 10, preferably 0.5 to 5 and in particular 0.8 to 2.5 percent by weight. Examples of hair cosmetics are hair strengtheners, hair rinses, compositions for stimulating hair growth, hair colorants, pre-treatment compositions, hair tonics, hairdressing creams, hairdressing gels, hair oils, hair pomades or hair brilliantines.

The quaternary ammonium salts which contain units of the formula (1) are preferably used as hair lacquers and hair sprays, in particular as aerosol sprays and especially as pump sprays, and also as shampoos and especially as setting lotions.

In addition to the quaternary ammonium salts which contain units of the formula (1), hair colorants as a rule also contain a carrier.

The carrier is preferably so chosen that a cream or a gel is obtained.

For oxidative colouring, the colorant can be in two parts, the second part being hydrogen peroxide. The two parts are mixed before use.

Hair cosmetics for pre-treatment, which are in the form of aqueous or aqueous-alcoholic solutions and if desired in aerosol flasks or in the form of a cream or gel, can be used for application prior to shampooing, especially prior to shampooing with an anionic and/or non-ionic shampoo, prior to oxidative colouring, which follows shampooing with an anionic and/or non-ionic shampoo, or prior to a permanent-wave treatment.

In these pre-treatment compositions, the quaternary ammonium salt containing units of the formula (1) is the active constituent and its concentration varies in general between 0.1 and 10 and especially between 0.2 and 5 percent by weight. The pH value of these compositions varies in general between about 3 and 9.

If the hair cosmetics are in the form of shampoos, they contain at least one detergent raw material (surfactant), and anionic, cationic, non-ionic and amphoteric compounds can be used. Cationic or non-ionic compounds are preferred.

Examples of anionic surfactants have already been mentioned above when defining the surfactant anions. Preferably, these surfactants are employed in excess, based on the cationic units of the formula (1), so that such surfactants are used simultaneously as the ion of opposite charge to the cationic units of the formula (1) and as the detergent raw material in the shampoos. These anionic surfactants and their mixtures are used in the form of their water-soluble or water-dispersible salts, for example in the form of the ether-sulfates, -sulfonates or -phosphates described above.

Suitable cationic surfactants are, for example, quaternary ammonium salts such as a dialkyl-dimethyl-ammonium chloride or dialkyl-dimethyl-ammonium bromide, an alkyl-dimethyl-ethyl-ammonium chloride or alkyl-dimethyl-ethyl-ammonium bromide, an alkyl-trimethyl-ammonium chloride or alkyl-trimethyl-ammonium bromide or an alkyl-dimethyl-benzyl-ammonium chloride or alkyl-dimethyl-benzyl-ammonium bromide, an N-alkyl-pyridinium chloride or N-alkyl-pyridinium bromide, salts of N,N-diethylaminoethyl-stearylamide and -oleylamide with hydrochloric acid, acetic acid or phosphoric acid and an N-acylamidoethyl-N,N-diethyl-N-benzyl-ammonium chloride, N-acylamidoethyl-N,N-diethyl-N-benzyl-ammonium bromide or N-acylamidoethyl-N,N-diethyl-N-benzyl-ammonium monoalkylsulfate, in which acyl is preferably the radical of stearic acid or oleic acid.

Examples of non-ionic surfactants which can be employed as detergent substances are: fatty alcohol ethoxylates, alkylphenyl polyethylene glycols, alkylaminopolyethylene glycols, fatty acid ethoxylates, fatty amine ethoxylates, polypropylene glycol ethoxylates, fatty acid amidopolyethylene glycols, sucrose esters or sorbitol esters. Non-ionic surfactants of particular interest are ethoxylated fatty amines, for example an ethoxylated tallow fatty amine.

Examples of amphoteric surfactants are betaines, such as an N-acylamidoalkyl-N,N-dimethyl-acetobetaine, preferably an N-acylamindopropyl-N,N-dimethyl-acetobetaine, or an alkyl-dimethyl-sulfopropyl-betaine(alkyl having 12 to 18 carbon atoms), amphoteric surfactants based on imidazoline, preferably the 1-($\beta$-carboxy-methoxyethyl)-1-(carboxymethyl)-b 2-lauryl-imidazolinium sodium salt, and amine oxides, for example alkyldimethylamine oxides (alkyl having 12 to 18 carbon atoms).

The hair cosmetics in the form of shampoos can, for example, additionally contain perfumes, dyes, preservatives, thickeners, foam stabilisers, softeners or a cosmetic resin.

As a rule, these shampoos contain about 0.8 to 2.5 parts by weight of at least one quaternary ammonium salt containing units of the formula (1) and about 10 to 20 parts by weight of at least one anionic, cationic, non-ionic or amphoteric detergent raw material of the type indicated above and are diluted with water, preferably deionised water, to a total of 100 parts by weight.

Hair lacquers, as hair cosmetics, are as a rule in the form of an alcoholic or aqueous-alcoholic solution of a cosmetic resin customary for lacquers and at least one quaternary ammonium salt containing units of the formula (1). They are applied as aerosol sprays with a propellant from an aerosol can or, preferably, as pump sprays.

If the hair cosmetics are in the form of an aerosol spray, they are as a rule anhydrous and contain ethanol or isopropanol as the solvent and additionally contain a propellant. Suitable propellants are, in particular, fluorinated and, if desired, chlorinated hydrocarbons having 1 to 4 and preferably 1 or 2 carbon atoms, such as octafluorobutane, tetrafluoromethane and trifluoromethane, for example dichlorotetrafluoroethane, dichlorodifluoroethane and in particular trichlorofluoromethane and dichlorodifluoromethane, and also lower alkanes, such as propane, isobutane and in particular butane. Preferably, mixtures of the compounds listed are employed.

Carbon dioxide can also be used successfully as the propellant gas. The latter, and in particular the lower alkanes, are preferred to the fluorinated hydrocarbons as propellants. For application as aerosol sprays, ammonium salts which contain a surfactant anion of the abovementioned type as the ion of opposite charge to the cationic units of the formula (1) are particularly preferred, because of their high solubility in ethanol or isopropanol.

As a rule, the aerosol sprays contain about 0.1 to 2.5 parts by weight of at least one quaternary ammonium salt containing units of the formula (1), about 15 to 65 parts by weight of at least one propellant gas of the indicated type and about 30 to 70 parts by weight of ethanol and/or isopropanol, so that the total amount makes up 100 parts by weight.

Setting lotions, as hair cosmetics, are especially suitable for hair which has become sensitive and contain at least one quaternary ammonium salt containing units of the formula (1), as a rule in aqueous or aqueous-alcoholic solution.

In addition, they can contain one or more cosmetic resins, especially homopolymers or vinyl copolymers, for example polyvinylpyrrolidone, the copolymers of polyvinylpyrrolidone and vinyl acetate, copolymers of crotonic acid and vinyl acetate or cellulose ethers containing quaternary nitrogen atoms, and as have been disclosed, for example, in U.S. Pat. No. 3,472,840.

If these lotions or setting lotions are in the form of aqueous solutions or of aqueous-alcoholic solutions which contain less than 5 to 10 percent by weight of an alcohol, they advantageously contain a preservative, for example an alkyl p-hydroxybenzoate, preferably methyl p-hydroxybenzoate.

The pH of these setting lotions is in general between 4.5 and 7.5. If desired, the pH value can be changed, for example by the addition of an alkanolamine, such as monoethanolamine or triethanolamine, or of an acid, such as hydrochloric acid or phosphoric acid or preferably acetic acid, lactic acid or citric acid.

If the hair cosmetics are in the form of setting lotions, they contain water and, if desired, ethanol or isopropanol as solvents. Preferably, the setting lotions contain about 0.8 to 25 parts by weight of at least one quaternary ammonium salt containing units of the formula (1) and 0 to about 70 parts by weight of ethanol and/or isopropanol and are diluted with about 30 to 99 parts by weight of water to give a total of 100 parts by weight.

If the hair cosmetics are in the form of a pump spray, they contain ethanol or isopropanol and, if desired, water as solvents. Preferably, the pump sprays contain about 0.8 to 2.5 parts by weight of at least one quaternary ammonium salt containing units of the formula (1) and 0 to about 10 parts by weight of water and are diluted to a total of 100 parts by weight with about 87 to 99 parts by weight of ethanol and/or isopropanol.

In the process, according to the invention, for the preparation of the hair cosmetics, at least one quaternary ammonium salt containing units of the formula (1) is mixed, preferably at room temperature, with the other components of the composition, for example a solvent of the indicated type, such as ethanol, isopropanol and/or water, and if desired a detergent raw material or a propellant and/or further additives of the indicated type.

The cosmetic treatment process according to the invention comprises applying to the hair a solution which contains ethanol, isopropanol and/or water as solvents and at least 0.01 percent by weight of at least one quaternary ammonium salt containing units of the formula (1). The solution, for example in the form of an aerosol spray or preferably of a pump spray, is sprayed onto the hair, or the solution is used for setting the hair.

When hair is immersed in or set or washed with the hair cosmetics in the form of setting lotions or shampoos, these compositions are applied to the hair at physiologically acceptable temperatures of preferably 20° to 45° C. The setting lotions are preferably applied to the hair so that the hair, which has been wetted with water, is impregnated at 20° to 45° C., rolled up on rollers and dried at 20° to 60° C. The shampoos are applied to the hair at 20° to 45° and preferably 20° to 40° C. and the shampoo is then preferably allowed to act on the hair for about 0.5 to 5 minutes. The hair is then rinsed at 20° to 45° C., rolled up to form curls and dried at about 20° to 60° C. The amount of shampoo is as a rule twice 5 to 10 ml per head of hair.

Human hair which is washed with a shampoo which contains the quaternary ammonium salts containing units of the formula (1) and then rinsed is, on the one hand, very easy to comb when wet and, on the other hand, in order to form curls, can be rolled up direct-i.e. without the use of an additional setting lotion-on rollers and then dried in air or with a hair dryer. After removing the rollers, the hair is very easy to style and has body and natural sheen as well as very good holding power, especially also in a damp climate. The shampoos thus display a double effect in that they serve on the one hand to clean the hair and, in addition, impart to the washed hair characteristics which make easy setting possible without necessitating the use of a special setting lotion (setting lotion/shampoo).

When the hair cosmetics are applied in the form of aerosol sprays or pump sprays, the hair is sprayed at room temperature and then dried, preferably at room temperature. Hair of natural or synthetic fibres, preferably human hair in the form of, for example, wigs or human hair in vivo, can be treated by the process according to the invention.

After they have been applied to the hair and after drying, the hair cosmetics according to the invention give a firm and continuous film, which is flexible, non-brittle, non-oily, non-greasy, colourless and transparent and is therefore also invisible and which imparts excellent holding power to the treated hair. The films obtained on the hair can be removed again without difficulty, with water, by vigorous brushing or preferably with hair shampoos. Surprisingly, however, the ease with which the films can be washed off has no adverse influence on the good shape-holding qualities of the treated hair, even when atmospheric humidity is high.

The ammonium salts which contain cationic units of the formula (1) are particularly suitable as washing agents for cationic dyeings, i.e. for textile materials which have been dyed or printed with cationic dyes.

Thus, the present invention also relates to a process for washing-off, in an aqueous medium, textile material which has been printed or dyed with at least one cationic dye, the material which is washed-off being printed or dyed material together with unprinted or undyed material, or materials which have each been printed or dyed with cationic dyes of different types, or a single material printed in parts, wherein the wash water contains at least one ammonium salt according to the invention, which contains cationic units of the formula (1).

The textile material washed-off according to the invention and the aqueous liquor, for carrying out the process according to the invention, which contains at least one ammonium salt of the indicated type are further subjects of the present invention.

Advantageously, 0.05 to 1.0 g and preferably 0.5 to 0.8 g of at least one of the ammonium salts according to the invention is used as the pure active substance per liter of wash water in the aqueous wash liquor. Washing-off is preferably carried out at elevated temperatures, for example of up to 100° C. and in particular 60° to 75° C. At high temperatures the washing time may be kept shorter. It is in general 5 to 60 minutes and in particular 10 to 20 minutes if washing-off is carried out at 60° to 75° C.

Printed or dyed textile materials which are washed-off according to the invention are, in particular, textile fibres, i.e. in particular synthetic fibres on their own or mixtures of synthetic and natural fibres, insofar at these fibres can be dyed with cationic dyes. Mixtures of different synthetic fibres can also be used.

These fibre materials are in very diverse stages of processing, for example in the form of tows, tops, filaments, yarns, woven fabrics, knitted fabrics, non-woven articles or finished articles of clothing.

Textile materials made of natural fibres which can be dyed with cationic dyes are, inter alia, those made of cellulosic materials, in particular of cotton, whilst the textile materials made of synthetic fibres are, for example, those made of high molecular weight modified polyesters, such as polyethylene terephthalate or polycyclohexanedimethylene terephthalate, of modified polyamides, such as polyhexamethylenediamine adipate, poly-$\epsilon$-caprolactam or poly-$\omega$-aminoundecanoic acid, of polyacrylonitriles or acrylonitrile copolymers and also of viscose, rayon, cellulose 1½-acetate and cellulose triacetate.

In particular, printed or dyed fibres of cellulose, preferably cotton, but also regenerated cellulose, such as viscose, or of modified polyester or polyamide which can be dyed with cationic dyes and, especially, printed or dyed modified acrylic or polyacrylonitrile fibres, are particularly suitable for washing-off according to the invention, and the fibres which have a rapid uptake can also be used. Modified polyester and polyamide fibres are described, for example, in Teintures et Apprêts 144, pages 163 to 167 (1974). Polyacrylonitrile fibres which have a rapid uptake are described, for example, in Melliand Textilberichte 12 (1968), pages 1436 to 1443, in J. Soc. Dyers and Colourists, May 1971, pages 149 to 155 and February 1978, pages 49 to 52, in Teintex 5 (1973), pages 281 to 296 and in Chemiefasern/Textilind. May 1974, pages 391 to 396 and January 1974, pages 52 to 60.

Modified acrylic fibres are fibres of acrylonitrile copolymers for the preparation of which yet further vinyl compounds, for example vinyl chloride, vinyl acetate, vinylidene chloride, vinylidene cyanide and alkyl acrylates, have been used in addition to acrylonitrile, insofar as the proportion of these other vinyl compounds is not greater than 20 percent, based on the weight of the materials.

In particular, printed or dyed polyacrylonitrile woven fabrics or knitted fabrics are especially suitable for washing-off by the process according to the invention.

Prior to washing-off by the process according to the invention, the textile materials are printed or dyed by conventional methods, dyeing preparations being employed which are in the form of aqueous and/or organic solutions or dispersions or in the form of printing pastes or printing inks and which contain, in addition to a dye, yet further additives, for example acids, salts, urea and further assistants such as oxalkylation products of fatty amines, fatty alcohols, alkylphenols, fatty acids and fatty acid amides. The cationic dyes which are used belong to very diverse groups. Suitable dyes are, for example, di- and tri-phenylmethane dyes, rhodamine dyes and azo or anthraquinone dyes containing onium groups, and also thiazine, oxazine, methine and azomethine dyes. These cationic dyes are described, for example, in the Colour Index, 3rd edition (1971), Volume 1, under the heading "Basic dyes".

According to the invention, it is possible, as already indicated, to wash-off printed or dyed textile material together with unprinted or undyed textile material. Staining of the with unprinted or undyed textile material by the dyes washed off from the printed or dyed material is prevented by the washing water according to the process of the invention containing an ammonium salt of the indicated type. In the case of the washing-off, according to the invention, of several materials, each of which has been printed or dyed with cationic dyes of different types, for example of blue printed material together with yellow printed material, cross-staining of the material with an undesired complementary dyeing, for example green dyeing, is also prevented. Preferably, according to the invention printed textile material, and especially a single textile material printed in parts, which has so-called coloured reserves or in particular white reserves, is washed-off. Due to the presence of ammonium salts in the washing water when the textile material printed in parts is washed-off by the process according to the invention, undesired restaining of the coloured reserves or white reserves is completely excluded. Moreover, the fastness to washing and to light of the dyed or printed textile material is increased.

The polymeric ammonium salts containing cationic units of the formula (1) also have interesting properties as paper sizes. Thus, a process for the engine sizing and in particular for the surface sizing of paper using the ammonium salts according to the invention, and the paper sized by this process, constitute further subjects of the invention.

Prior to their use as paper sizes, the ammonium salts according to the invention are so diluted with water that aqueous size liquors are formed, the content of which, calculated for the pure active substance, is 0.02 to 1 and preferably 0.02 to 0.2 percent by weight. In the case of engine sizing, 0.3 to 4 percent by weight of the ammonium salt, calculated for pure active substance and based on the solids content of the paper to be made, with the inclusion of binders, such as starch, are incorporated in the form of the dilute size liquor into the fibre suspension upstream of the headbox of the papermaking machine. In the case of the preferred surface sizing, the paper is impregnated with the dilute size liquor, in general at room temperature, for example by spraying or in particular by padding, and is then dried at 60° to 140° and preferably at 90° to 110° C. for 0.1 to 10 and preferably 1 to 6 minutes. After drying, coatings of the ammonium salts, calculated as pure active substance, per unit surface area of 50 to 150 and preferably 60 to 120 mg/m$^2$ are obtained.

Even with small amounts of ammonium salts according to the invention, very good sizing effects can be achieved on paper and these effects are confirmed on the basis of positive test results, such as water absorption measured by the Cobb method and alkaline ink flotation time. In particular, in the case of the preferred surface sizing, the small amounts applied per unit surface area make a rapid procedure possible, so that at a drying temperature of, for example, 90° to 110° C. good sizings are already achieved within about 20 to 40 seconds. Moreover, as a rule ammonium salts do not tend to undesirable foaming.

By virtue of their cationic units of the formula (1), the ammonium salts according to the invention are also suitable for use as fixing agents when dyeing cellulose-containing materials with appropriate anionic dyes. A process for the after-treatment of cellulse-containing materials, which have been dyed with anionic dyes, by means of the ammonium salts according to the invention, preferably in the form of an aqueous, dilute solution thereof, thus constitutes a further subject of the invention. The materials are in particular fibre materials, for example textile fibres in the very diverse stages of processing indicated above, and these may be in a mixture with synthetic fibres of, for example, polyester, polyamide or polyacrylic fibres, such as cotton/polyester mixed fabric, but preferably consist of textile fibres of cellulose, which can be regenerated, on its own, such as viscose, rayon and preferably cotton. Preferred cellulose-containing materials are, however, wood and in particular cardboard or paper. The anionic dyes employed are in particular water-soluble, substantive, direct dyes. Such dyes are described, inter alia, in the chapter "Direct dyes" in the textbook "Künstliche organische Farbstoffe und ihre Zwischen-produkte" ("Synthetic organic dyes and their intermediates") by H. R. Schweizer, Springer Verlag Berlin (1964), pages 481 to 495. Amongst these dyes, suitable dyes are in particular azo dyes, especially disazo or triazo dyes, which contain anionic sulfonic acid groups conferring solubility in water. The triazinyl dyes are of particular importance.

In the embodiment of the dyeing process according to the invention which is of primary interest, the paper is preferably dyed in the pulp, i.e. in the fibre suspension before this is worked up to give finished paper products. For this purpose, as a rule 0.01 to 1, preferably 0.02 to 1 and in particular 0.08 to 0.7 percent by weight of the abovementioned dyes, calculated as the anydrous and extender-free dye, based on the dry fibre content of the fibre suspension, and 0.05 to 3, preferably 0.2 to 0.8 and in particular 0.4 to 0.8 percent by weight of the ammonium salts according to the invention, calculated as the pure active substance, based on the dry fibre content of the fibre suspension, are added to the fibre suspension.

In the process for the pulp-dyeing of paper, first the dye and then the ammonium salt are added to the fibre suspension, the dye being added preferably 20 to 120 and in particular 30 to 40 minutes and the ammonium salt being added preferably 3 to 300, preferentially 10 to 120 and in particular 5 to 45 seconds before the pulp enters the headbox of the papermaking machine.

The fibre suspension to which the dyes and ammonium salts are added is in general neutral to weakly alkaline or weakly acid, has as a rule a pH value of 6 to 8 or of 7 to 8, a dry fibre content of 0.1 to 4.5, preferably 0.6 to 1.5 and in particular 0.2 to 1.2 percent by weight and a Schopper-Riegler freeness of 20° to 60°, preferably 30° to 50° and in particular 25° to 35° and as a rule contains sulfite pulp, preferably soft wood sulfite pulp, sulfate pulp, preferably beech sulfate pulp, and, if desired, groundwood.

The fibre suspension can also contain organic or mineral fillers. Suitable organic fillers are, inter alia, synthetic pigments, for example polycondensation products of urea or melamine and formaldehyde which have large specific surface areas and are in a highly dispersed form, these products being described, inter alia, in British Patent Specifications Nos. 1,043,937 and 1,318,244, and suitable mineral fillers are, inter alia, talc, titanium dioxide and in particular kaolin and/or calcium carbonate. As a rule, the fibre suspension contains 0 to 40 and preferably 5 to 15 percent by weight, based on the dry fibre content, of fillers of the indicated type.

When, for example, calcium carbonate is added, in general weakly alkaline fibre suspensions are obtained but, on the other hand, when, for example, kaolin is added, in general weakly acid fibre suspensions are obtained.

In the process according to the invention, the fibre suspension is further processed in a manner known per se, sheet formers or preferably continuously on papermaking machines of conventional construction, to give paper or cardboard. Thus, paper or cardboard dyed using the process according to the invention constitutes a further subject of the present invention. These products are distinguished by their particularly fast dyeings, which in particular have good fastness to water and especially good fastness to light.

The good algicidal, fungicidal and bactericidal properties of the ammonium salts, according to the invention, containing cationic units of the formula (1) can be utilised, for example, in processes for water treatment or for the treatment of substrates and these processes are further subjects of the invention. These processes comprise adding the ammonium salts to the water to be treated or applying the ammonium salts, if desired in the form of an organic-aqueous finely dispersed emulsion, to the substrates.

In the examples which follow, parts and percentages are by weight.

EXAMPLE 1

40.5 parts (0.043 mol) of a diepoxide with an epoxide equivalent weight of 467, which has the formula

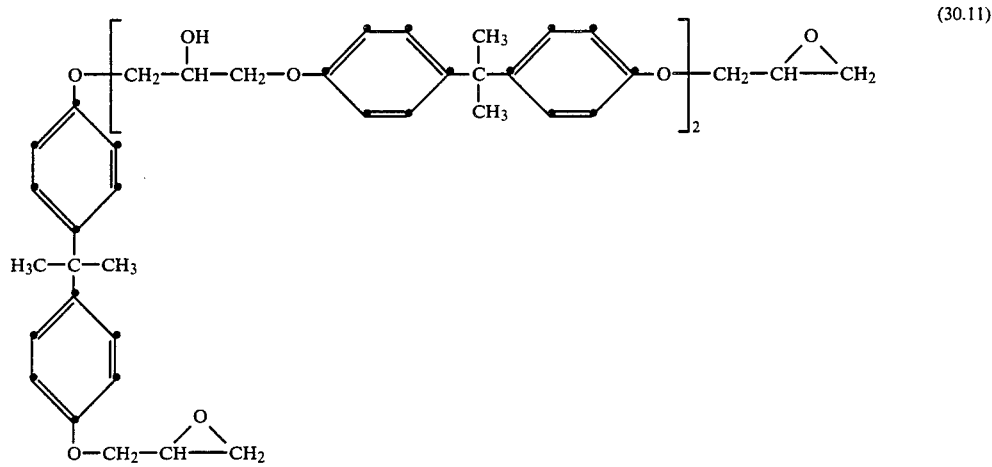

(30.11)

and 13.05 parts (0.043 mol) of 1.3-bis-(3'-dimethylaminopropyl)-urea dihydrochloride are dissolved in 250 parts of 1-methoxy-2-ethanol and reacted for 5 hours at 120° to 125° C.

After the reaction has ended, the solvent is distilled off at about 80° C. and under a reduced pressure of about 0.2 bar. For better handling, the viscous distillation residue is diluted with a 1:1 mixture of methanol, ethanol or isopropanol and deionised water to give a solution which contains 10% of an ammonium salt which contains cationic units of the formula (29.1) and in which 2Cl$^\ominus$ are present as anions. However, it is also possible to introduce the distillation residue into 1,000 parts of acetone and to separate off the resulting white precipitate by filtration and to dry it under reduced pressure at 60° C.

EXAMPLE 2

The procedure of Example 1 is repeated except that 16.3 parts (0.043 mol) of a diepoxide with an epoxide equivalent weight of 189, which has the formula

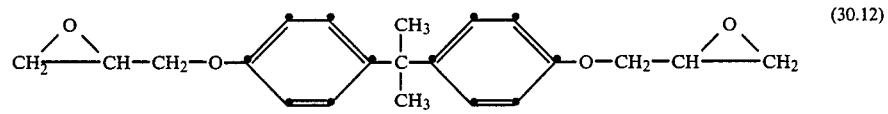

(30.12)

are employed.

The dilute 10% solution in a 1:1 mixture of water: methanol, ethanol or isopropanol contains an ammonium salt which contains cationic units of the formula (29.2) and in which 2Cl$^\ominus$ are present as anions.

EXAMPLE 3

40.5 parts (0.043 mol) of the diepoxide of the formula (30.11) indicated in Example 1 and 15.05 parts (0.043 mol) of the salt of 1,3-bis-(3'-dimethylaminopropyl)-urea and acetic acid are introduced into 400 parts of water and reacted for 20 hours at 90°–95° C., 100 parts of water being distilled off from the reaction mixture in the course of the reaction. For working up, the reaction mixture is introduced into 4,500 parts of acetone, and the ammonium salt precipitated in this way is separated off by filtration and dried under reduced pressure at 70° C. An ammonium salt is obtained which contains cationic units of the formula (29.1) and in which 2⊖OO-C—CH₃ are present as anions.

EXAMPLE 4

40.5 parts (0.043 mol) of the diepoxide of the formula (30.11) indicated in Example 1 and 27.9 parts (0.043 mol) of the salt of 1,3-bis(3′-dimethyl-amino-propyl)-urea and lauric acid are dissolved in 350 parts of 1-methoxy-2-ethanol and reacted for 5 hours at 125° C. For working up, the reaction mixture is introduced into 4,000 parts of acetone and the ammonium salt which has precipitated is separated off by filtration and dried under reduced pressure at 70° C. An ammonium salt is obtained which contains cationic units of the formula (29.1) and in which 2⊖OOC—(CH₂)₁₀—CH₃ are present as anions.

EXAMPLE 5

123.6 parts of the ammonium salt according to Example 1, which has been precipitated with acetone and contains cationic units of the formula (29.1) and in which 2Cl⊖ are present as anions, are dissolved in 650 parts of water and 100 parts of ethanol. A solution of 30.6 parts of sodium stearate in 1,200 parts of ethanol and 300 parts of water is added to this solution. The reaction mixture is concentrated to 1,000 parts at 60° C. under reduced pressure, whereupon the ammonium salt precipitates. After adding 2,000 parts of water, the ammonium salt is separated off by filtration and dried under reduced pressure at 50° C. An ethanol-soluble ammonium salt is obtained which contains cationic units of the formula (29.1) and in which about 50% of the 2Cl⊖ anions originally present have been replaced by ⊖OOC—(CH₂)₁₆—CH₃.

Example 6

123.6 parts of the ammonium salt according to Example 1, which has been precipitated with acetone, are dissolved in 1,500 parts of water. A solution of 58.8 parts of sodium lauryl-sulfate in 500 parts of water is added to this solution in the course of 30 minutes, with vigorous stirring, the ammonium salt precipitating at the same time. The ammonium salt is separated off by filtration and dried under reduced pressure at 60° C. As a result of the quantitative replacement of the chloride ions originally present by lauryl-sulfate ions, the resulting ammonium salt contains cationic units of the formula (29.1) and contains 2⊖SO₃—O—(CH₂)₁₁—CH₃ as anions.

EXAMPLE 7

The procedure of Example 1 is repeated, except that 17.1 parts of the epoxide of the formula (30.12) indicated in Example 2 are employed (0.045 mol or an epoxide:diamine molar ratio of 1:0.95). The ammonium salt which contains cationic units of the formula (29.2) and in which 2Cl⊖ are present as anions is obtained.

EXAMPLE 8

The procedure of Example 1 is repeated, except that 15.5 parts of the epoxide of the formula (30.12) indicated in Example 2 are employed (0.041 mol or an epoxide:diamine molar ratio of 1:1.05). The ammonium salt which contains cationic units of the formula (29.2) and in which 2Cl⊖ are present as anions is obtained.

EXAMPLE 9

The procedure of Example 1 is repeated, except that 16.3 parts (0.043 mol) of the diepoxide of the formula (30.12) indicated in Example 2 and 15.5 parts (0.043 mol) of the di-tertiary amine salt of the formula

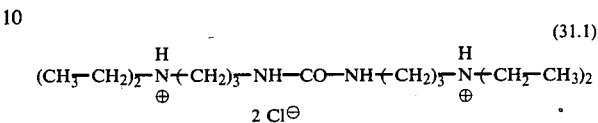

are employed. An ammonium salt is obtained which contains cationic units of the formula (29.3) and in which 2Cl⊖ are present as anions.

EXAMPLE 10

The procedure of Example 1 is repeated, except that 16.3 parts (0.043 mol) of the diepoxide of the formula (30.12) indicated in Example 2 and 11.9 parts (0.043 mol) of the di-tertiary amine salt of the formula

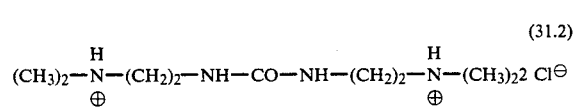

are employed. An ammonium salt is obtained which contains cationic units of the formula (29.4) and in which 2Cl⊖ are present as anions.

EXAMPLE 11

The procedure of Example 1 is repeated, except that 16.3 parts (0.043 mol) of the diepoxide of the formula (30.12) indicated in Example 2 and 11.2 parts (0.043 mol) of the di-tertiary amine salt of the formula

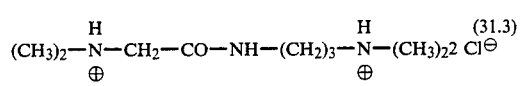

are employed. An ammonium salt is obtained which contains cationic units of the formula (29.5) and in which 2Cl⊖ are present as anions.

EXAMPLE 12

The procedure of Example 1 is repeated, except that 16.3 parts (0.043 mol) of the diepoxide of the formula (30.12) indicated in Example 2 and 14.3 parts (0.043 mol) of the di-tertiary amine salt of the formula

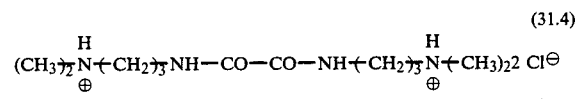

are employed. A quaternary ammonium salt is obtained which contains cationic units of the formula (29.6) and in which 2Cl⊖ are present as anions.

EXAMPLE 13

The procedure of Example 1 is repeated, except that 16.3 parts (0.043 mol) of the diepoxide of the formula (30.12) indicated in Example 2 and 16.7 parts (0.043 mol) of the di-tertiary amine salt of the formula

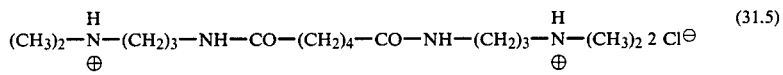

are employed. An ammonium salt is obtained which contains cationic units of the formula (29.7) and in which 2Cl⊖ are present as anions.

EXAMPLE 14

The procedure of Example 1 is repeated, except that 16.3 parts (0.043 mol) of the diepoxide of the formula (30.12) indicated in Example 2 and 17.6 parts (0.043 mol) of the di-tertiary amine salt of the formula

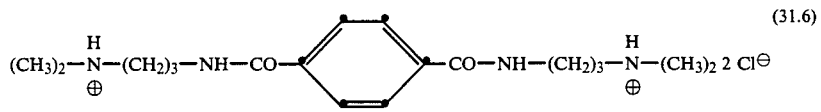

are employed. An ammonium salt is obtained which contains cationic units of the formula (29.8) and in which 2Cl⊖ are present as anions.

EXAMPLE 15

The procedure of Example 1 is repeated, except that 16.3 parts (0.043 mol) of the diepoxide of the formula (30.12) indicated in Example 2 and 17.6 parts (0.043 mol) of the di-tertiary amine salt of the formula

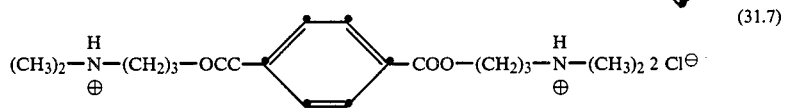

are employed. A quaternary ammonium salt is obtained which contains cationic units of the formula (29.9) and in which 2Cl⊖ are present as anions.

EXAMPLE 16

The precedure of Example 1 is repeated, except that 16.3 parts (0.043 mol) of the diepoxide of the formula (30.12) indicated in Example 2 and 16.0 parts (0.043 mol) of the di-tertiary amine salt of the formula

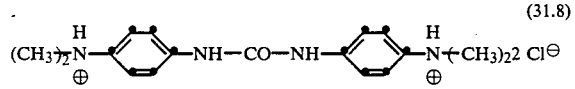

are employed. An ammonium salt is obtained which contains cationic units of the formula (29.10) and in which 2Cl⊖ are present as anions.

EXAMPLE 17

The procedure of Example 1 is repeated, except that 16.3 parts (0.043 mol) of the diepoxide of the formula (30.12) indicated in Example 2 and 16.5 parts (0.043 mol) of the di-tertiary amine salt of the formula

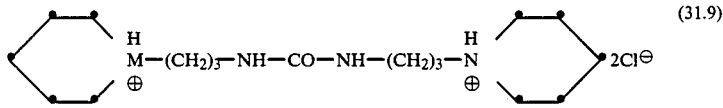

are employed. As ammonium salt is obtained which contains cationic units of the formula (29.11) and in which 2Cl⊖ are present as anions.

Example 18

The procedure of Example 1 is repeated, except that 16.3 parts (0.043 mol) of the diepoxide of the formula (30.12) indicated in Example 2 and 14.5 parts (0.043 mol) of the di-tertiary amine salt of the formula

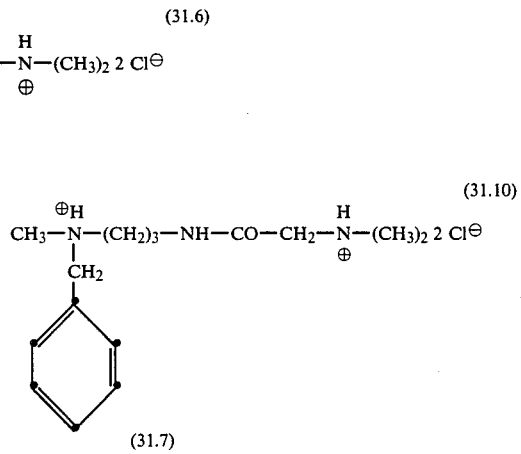

are employed. An ammonium salt is obtained which contains cationic units of the formula (29.12) and in which 2Cl⊖ are present as anions.

EXAMPLE 19

The procedure of Example 1 is repeated, except that 8.8 parts (0.043 mol) of a diepoxide with an epoxide equivalent weight of 102, which has the formula

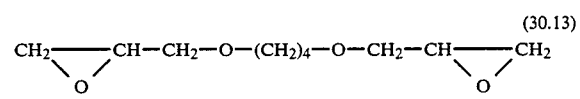

and 13.05 parts (0.043 mol) of 1,3-bis-(3'-dimethylaminopropyl)-urea dihydrochloride are employed. A quaternary ammonium salt is obtained which contains cationic units of the formula (29.13) and in which 2Cl⊖ are present as anions.

EXAMPLE 20

The procedure of Example 1 is repeated, except that 8.8 parts (0.043 mol) of the epoxide of the formula (30.13) indicated in Example 19 and 14.3 parts (0.043 mol) of the di-tertiary amine salt of the formula (31.4) indicated in Example 12 are employed. An ammonium salt is obtained which contains cationic units of the formula (29.14) and in which 2Cl⊖ are present as anions.

EXAMPLE 21

The procedure of Example 1 is repeated, except that 12.0 parts (0.043 mol) of a diepoxide with an epoxide equivalent weight of 139, which has the formula

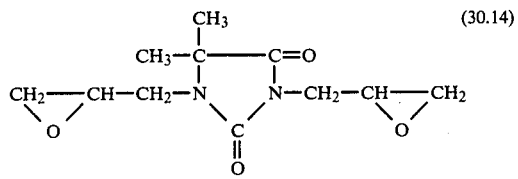

(30.14)

and 16.7 parts (0.043 mol) of the di-tertiary amine salt of the formula (31.5) indicated in Example 13 are employed. An ammonium salt is obtained which contains cationic units of the formula (29.15) and in which 2Cl⊖ are presents as anions.

EXAMPLE 22

The procedure of Example 1 is repeated, except that 15.7 parts (0.043 mol) of a diepoxide with an epoxide equivalent weight of 170, which has the formula

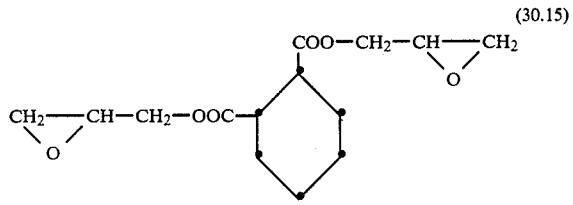

(30.15)

and 13.05 parts (0.043 mol) of 1,3-bis-(3'-dimethylaminopropyl)-urea dihydrochloride are employed. An ammonium salt is obtained which contains cationic units of the formula (29.16) and in which 2Cl⊖ are present as anions.

EXAMPLE 23

The procedure of Example 1 is repeated, except that 17.2 parts (0.043 mol) of a diepoxide with an epoxide equivalent weight of 200, which has the formula

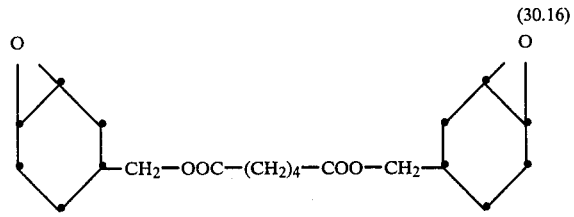

(30.16)

and 13.05 parts (0.043 mol) of 1,3-bis-(3'-dimethylaminopropyl)-urea dihydrochloride are employed. An ammonium salt is obtained which contains cationic units of the formula (29.17) and in which 2Cl⊖ are present as anions.

EXAMPLE 24

The procedure of Example 1 is repeated, except that 11.6 parts (0.043 mol) of a diepoxide with an epoxide equivalent weight of 135, which has the formula

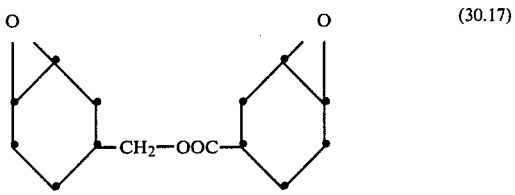

(30.17)

and 13.05 parts (0.043 mol) of 1,3-bis-(3'-dimethylamino-propyl)-urea dihydrochloride are employed. An ammonium salt is obtained which contains cationic units of the formula (29.18) and in which 2Cl⊖ are present as anions.

EXAMPLE 25

The procedure of Example 1 is repeated, except that 13.8 parts (0.043 mol) of a diepoxide with an epoxide equivalent weight of 160, which has the formula

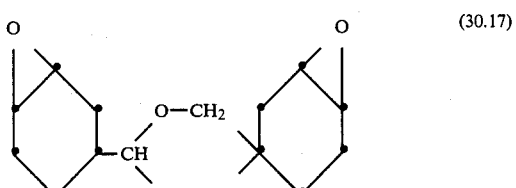

(30.17)

and 14.3 parts (0.043 mol) of the di-tertiary amine salt of the formula (31.4) indicated in Example 12 are employed. An ammonium salt is obtained which contains cationic units of the formula (29.19) and in which 2Cl⊖ are present as anions.

EXAMPLE 26

The procedure of Example 1 is repeated, except that 7.85 parts (0.043 mol) of a diepoxide with an epoxide equivalent weight of 91, which has the indicated formula (30.5), and 13.05 parts (0.043 mol) of 1,3-bis-(3'-dimethylaminopropyl)-urea dihydrochloride are employed. An ammonium salt is obtained which contains cationic units of the formula (29.20) and in which 2Cl⊖ are present as anions.

EXAMPLE 27

A 10% solution of an ammonium salt which contains cationic units of the formula (29.2) and in which 2Cl⊖ are present as anions is evaporated to dryness under reduced pressure and dried at 70° C. and 0.05 mm Hg. The resulting hydroscopic, brittle powder (27.7 parts) is suspended in 120 parts of tetrahydrofuran. 0.2 part of 4-dimethylaminopyridine and 13.3 parts of acetic anhydride (0.13 mol or 3 mols per mol of ammonium salt employed) are added to this suspension. The reaction mixture is heated to the reflux temperature of about 70° C. and kept at this temperature for 5 hours. After this time, 300 parts of ethanol are added to the reaction mixture. The reaction mixture is then heated to the reflux temperature of about 80° C. and kept at this temperature for a further 2 hours, during which time a clear solution forms from the original suspension; this solution is evaporated to dryness under reduced pressure. After drying the residue at 70° C. and 0.05 mm Hg, 36.3 parts of an ammonium salt are obtained which contains cationic units of the formula (29.21) and in which 2Cl$^\ominus$ are present as anions; this salt is in the form of a water-soluble, yellowish powder.

EXAMPLE 28

10 parts of the ethanolic solution of the quaternary ammonium salt obtained according to Example 1 are mixed with 25 parts of ethanol (96%) and 65 parts of deionised water to give a total of 100 parts of a hair cosmetic setting lotion, the pH value of which is adjusted to 6.0 with lactic acid.

Human hair which has been wetted with water is impregnated with this setting lotion at room temperature and then rolled up on rollers and dried at room temperature.

The hair has an invisible film which imparts an excellent hold quality to the hair after removal of the rollers, this hold being retained even in a damp climate.

The film can be removed easily on washing the hair with commercially available shampoos.

Similar results are obtained with the quaternary ammonium salt obtained according to Example 2.

EXAMPLE 29

20 parts of the ethanolic solution of the quaternary ammonium salt obtained according to Example 1 are mixed with 50 parts of ethanol (96%) and 10 parts of deionised water to give a total of 100 parts of a hair cosmetic pump spray.

Styled human hair is sprayed at room temperature using a hand atomiser. After a drying time of about 1 minute at room temperature, the styled hair has an invisible film which imparts an excellent hold quality to the hair, this hold being retained even when the hair is damp.

Similar results are obtained with the quaternary ammonium salt obtained according to Example 2.

EXAMPLE 30

1 part of the ammonium salt obtained according to Example 4 is dissolved in 39 parts absolute alcohol. 60 parts of a propellant which consists of a 1:1 mixture of dichlorotetrafluoroethane and dichlorodifluoroethane are added to this solution in an aerosol can. Human hair treated with this aerosol spray has excellent hold qualities, which are retained even in a damp climate. The polymer sprayed onto the hair can be removed easily on washing the hair with commercially available shampoos.

EXAMPLE 31

A polyacrylonitrile fabric is printed in parts with an aqueous printing paste which contains 2.5% of the red dye of the formula

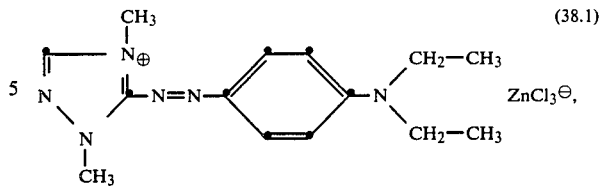

3% of a 10% condensation product of a naphthalenesulfonic acid and formaldehyde and 94.5% of an aqueous stock solution of a thickener.

The aqueous stock solution of the thickener contains 50% of a 16%, neutral, non-ionic carob bean flour ether, 3% of a 50% tartaric acid and 15% of N,N-bis-(cyanoethyl)-formamide.

After printing, the fabric is dried and treated with saturated steam at 110° C. for 30 minutes in order to fix the print.

The polyacrylonitrile fabric printed in this way is now washed-off for 20 minutes at 75° C. in an aqueous liquor which contains 0.05 g/l, based on active substance, of the ammonium salt according to Example 2.

The fabric which has been washed-off displays sharp red patterns, and the areas which have not been printed (white reserve) remain completely unstained. If, on the other hand, the fabric is washed-off with water in the absence of the ammonium salt under identical conditions, the unprinted areas of the fabric have an undesired pink coloration due to bleeding of the dye.

Moreover, the printed fabric washed-off according to the invention in the presence of the ammonium salt is, according to DIN 54,010, 54,006 and 54,004, fast to washing and to light, which is not the case for printed fabrics which have not been washed-off or which have been washed-off in the absence of the ammonium salt.

Similar results are obtained with the ammonium salts according to one of Examples 1 or 3 to 27.

EXAMPLE 32

A filterpaper of pure cellulose with a weight per unit area of 110 g/m$^2$ are padded at a speed of 4 m/minute and with a contact pressure of 10 bars with an aqueous liquor which contains 0.1%, based on active substance, of the ammonium salt according to Example 1. The padded paper is dried for 10 minutes at 90° C. The surface sizing obtained on the treated paper is tested on the basis of the Cobb water absorption test, with a time of action of 30 seconds, (WA Cobb$_{30}$) in accordance with DIN 53,132. The lower the water absorption in the WA Cobb$_{30}$ test, the better is the surface sizing of the treated paper. In this test, the WA Cobb$_{30}$ of the paper treated according to the invention is 20 g/m$^2$, whilst untreated paper has a WA Cobb$_{30}$ of 188 g/m$^2$.

EXAMPLE 33

In a mixing chest, 10% of precipitated calcium carbonate, in the form of a 30% aqueous suspension, are added to a fibre suspension which consists of 50% of bleached soft wood sulfite pulp and 50% of bleached beech sulfate pulp and has a Schopper-Riegler freeness of 22°. The pH value of the fibre suspension adjusts to 7.4 to 7.5 after the addition of the calcium carbonate.

The fibre suspension is diluted continuously with water to a dry fibre content of 1.2%.

0.13% of the dye of the formula

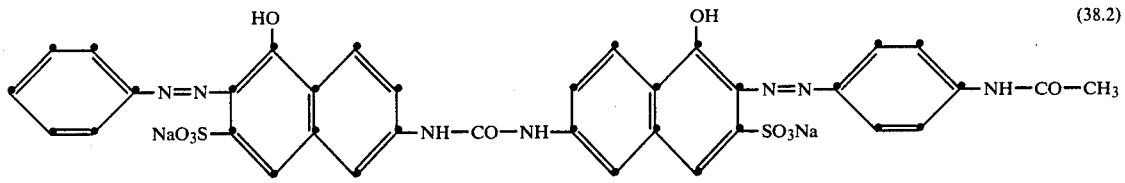

(38.2)

is added to the fibre suspension 30 minutes before the latter enters the headbox of the papermaking machine. 1.5%, based on active substance, of the ammonium salt according to Example 1 are then added to the fibre suspension about 25 seconds before the latter enters the headbox of the papermaking machine.

The fibre suspension is processed in a laboratory papermaking machine with a constant machine setting to give a paper which has a weight per unit area of 75±2 g/m². The paper is dried in the machine in such a way that the paper retains a residual moisture content of 5%. The resulting paper sheets are conditioned for 24 hours at 65% relative atmospheric humidity.

The dyed paper produced in this way has good fastness to light and to water.

EXAMPLE 34

A phosphate buffer medium (pH 5, 7 and 8) which contains 1,000 ppm of the ammonium salt according to Example 7 is inoculated with, in each case, one test strain (bacteria: 0/n cultures; fungi: spore suspension, 14-day cultures) (final concentration $10^6$ germs/ml). After an incubation time of 18 hours at 20° C. on a magnetic stirrer tests are carried out to determine at which concentration killing of the germs has taken place.

In this test, the ammonium salt tested shows a good germicidal action.

The test germs used are:
*Staphylococcus aureus:* ATCC 6538
*Escherichia coli:* ATCC 11229
*Pseudomona aeruginosa:* ATCC 15442
*Aspergillus niger:* ATCC 6275.

Medium: Sörensen phosphate buffer (1/15 molar) with 2% brain-heart infusion broth.

In this test, the ammonium salts according to one of Examples 1 to 6 and 8 to 27 likewise have good bactericidal and fungicidal properties.

What is claimed is:

1. A process for the treatment of water, which comprises adding to the water to be treated an effective amount of an ammonium salt as an algicide, bactericide or fungicide, said ammonium salt consisting essentially of cationic units which contain diepoxide and diamine radicals and having the formula

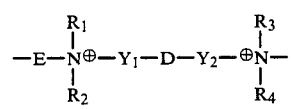

in which E is a divalent bridge member which has one of the formulae

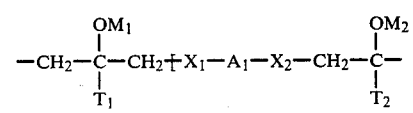

-continued

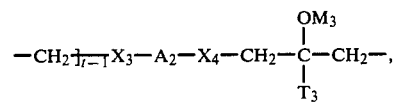

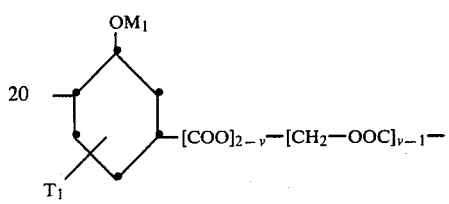

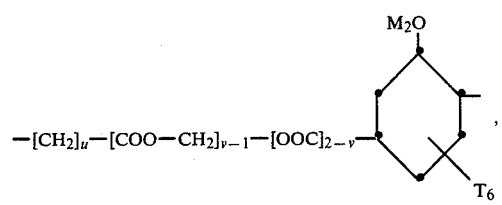

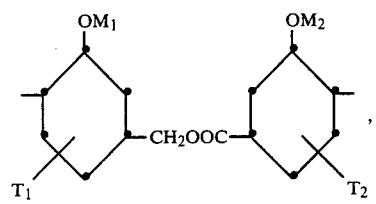

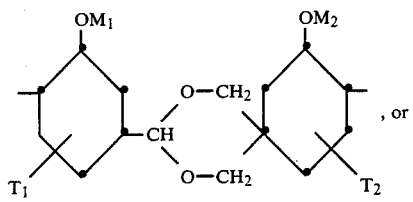

, or

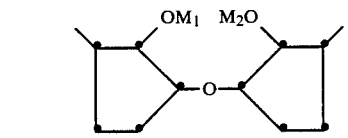

in which t is a number from 1 to 4, u is an integer from 1 to 8 and v is 1 or 2 and $R_1$, $R_2$, $R_3$ and $R_4$ are identical or different and are alkyl, cycloalkyl or alkenyl having not more than 8 carbon atoms, which radicals are unsubstituted or substituted by hydroxyl, alkoxy, alkylthio or cyano, or aryl or aralkyl, which are unsubstituted or substituted by hydroxyl, hydroxyalkyl, alkoxy, alkoxyalkyl, alkyl alkylthio, cyano or halogen, or ($R_1$ and $R_2$) and/or ($R_3$ and $R_4$) together with the nitrogen atom to which they are bonded form a piperidine ring, $M_1$, $M_2$ and $M_3$ are each acyl having 2 to 5 carbon atoms or hydrogen, $Y_1$ and $Y_2$ are identical or different from one another and have the formula —$C_mH_{2m}$— in which m is an integer from 1 to 12, the sum of the m's in $Y_1$ and $Y_2$ is not less than 3 and when m is 1 the bond to the bridge member D is not made via a nitrogen atom or oxygen atom, or $Y_1$ and $Y_2$ are phenylene, which is unsubtituted or substituted by halogen, hydroxyl, alkyl, halogenoalkyl, hydroxyalkyl or alkoxy, D is a divalent bridge member of one of the formula

—NHCONH—, —NHCOD$_1$CONH—, —CONH—,

—OCONH—, —COO—, —COD$_2$CO—,

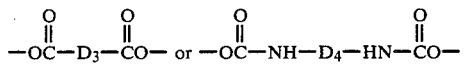

in which $D_1$ is a direct bond, alkylene, alkenylene, arylene, heteroarylene, diaminoalkylene, diaminoarylene or unsubtituted or halogen-substituted dioxyalkylene, polyoxyalkyleneoxy or dioxyarylene, $D_2$ is diaminoalkylene or unsubstituted or halogen-substituted dioxyalkylene, polyoxyalkyleneoxy or dithioalkylene, $D_3$ is arylene and $D_4$ is alkylene or arylene, $T_1$, $T_2$ and $T_3$ are each hydrogen or methyl, $X_1$, $X_2$, $X_3$ and $X_4$ are each —COO—, —OOC—, —O— or a direct bond and $A_1$ and $A_2$ are each a heterocyclic ring which has 5 or 6 ring members and 2 nitrogen atoms and can be substituted in alkyl, or alkylene which can be interrupted by hetero-atoms, or cycloalkylene, cycloalkenylene, arylene or aralkylene which have 1 or 2 rings and can be substituted by alkyl or halogen, the bridge members in ring form being bonded via a direct bond, via a heteroatom or via an alkylene bridge, which can be interrupted by hetero-atoms.

2. A process according to claim 1 wherein the ammonium salt consists essentially of cationic units of the formula

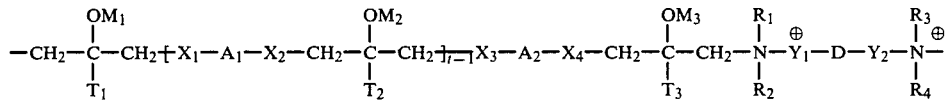

in which $A_1$ and $A_2$, D, $M_1$, $M_2$, $M_3$, $R_1$, $R_2$, $R_3$, $R_4$, $T_1$, $T_2$, $T_3$, $X_1$, $X_2$, $X_3$, $X_4$, $Y_1$, $Y_2$ and t are as defined in claim 1.

3. A process according to claim 1 wherein the ammonium salt consists essentially of cationic units of one of the formulae

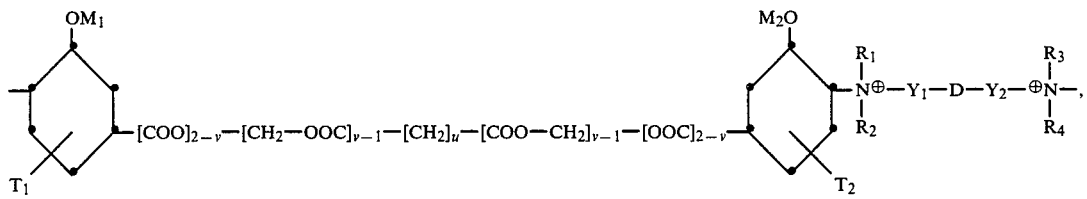

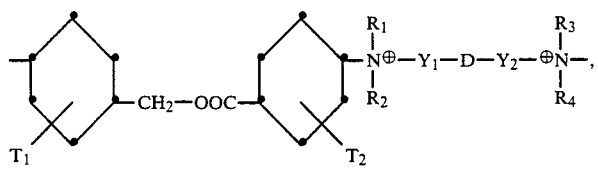

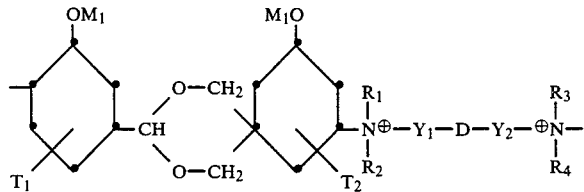

or

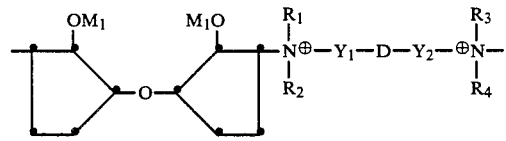

in which D, $M_1$, $M_2$, $R_1$, $R_2$, $R_3$, $R_4$, $T_1$, $T_2$, $Y_1$, $Y_2$, u and v are as defined in claim 1.

4. A process according to claim 1 wherein the ammonium salt consists essentially of cationic units of one of the formula

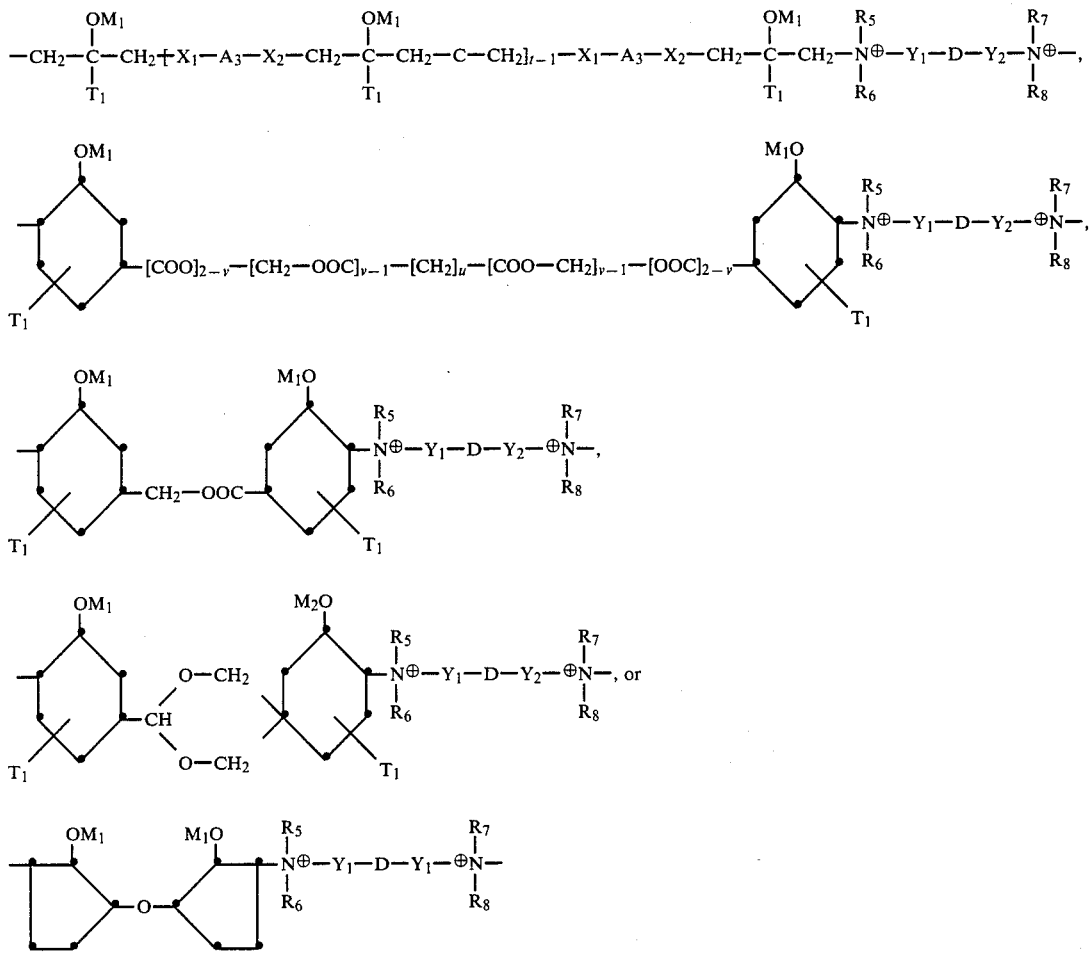

in which $R_5$, $R_6$, $R_7$ and $R_8$ are identical to or different from one another and are alkyl, hydroxyalkyl, alkoxyalkyl, alkylthioalkyl or cyanoalkyl having a total of 1 to 8 carbon atoms, cyclopentyl, cyclohexyl, alkenyl having 2 to 4 carbon atoms, unsubstituted phenyl or benzyl, or phenyl or benzyl substituted by hydroxyl, cyano, chlorine, bromine or alkyl, hydroxyalkyl, alkoxy, alkylthio or alkoxyalkyl each having 1 or 2 carbon atoms in the alkyl moiety and alkoxy moiety; or ($R_5$ and $R_6$) and ($R_7$ and $R_8$), together with the nitrogen atom to which they are bonded, form a piperidine ring, wherein $A_3$ is a heterocyclic ring having 5 or 6 ring members and 2 nitrogen atoms, which is unsubstituted or substituted by methyl, ethyl or isopropyl, or alkylene having 2 to 34 carbon atoms, which can be interrupted by oxygen atoms, cycloalkenylene having 6 to 10 carbon atoms, which can be substituted by methyl or ethyl, or cycloalkylene which has one or two rings and has 6 to 18 carbon atoms or arylene which has one to two rings and has 6 to 18 carbon atoms or aralkylene which has one or two rings and has 8 to 26 carbon atoms, the two latter radicals being unsubstituted or substituted by bromine or chlorine, and D, $M_1$, $T_1$, $X_1$, $X_2$, $Y_1$, $Y_2$, t, u and v are as defined in claim 1.

5. A process according to claim 1 wherein the ammonium salt according to claim 1 consists essentially of cationic units of one of the formulae

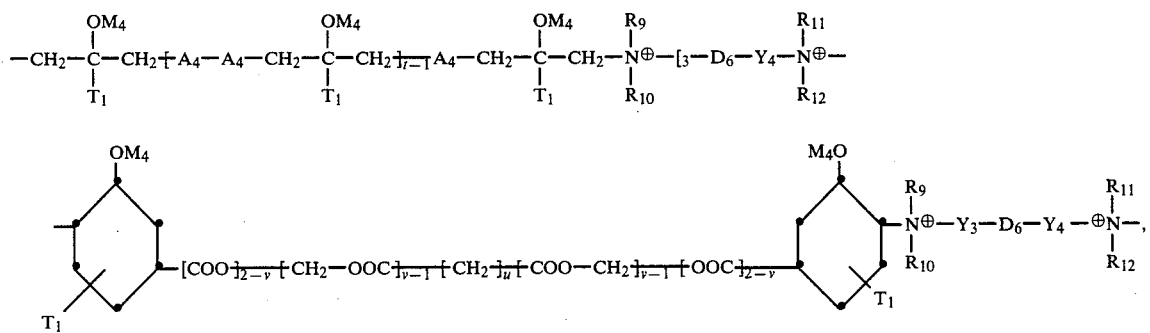

-continued

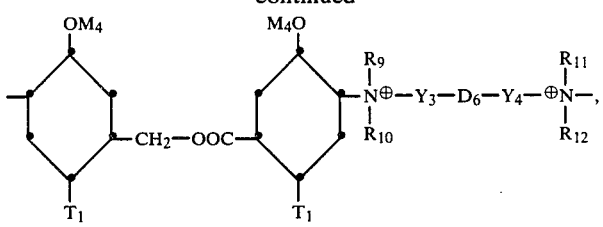

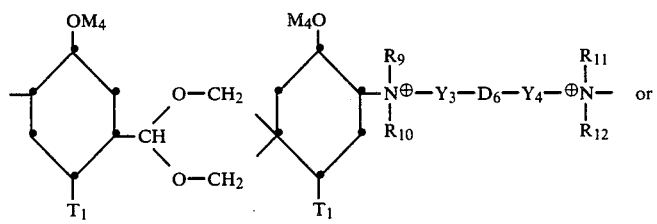

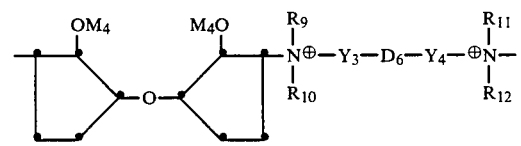

in which $D_6$ has one of the formulae

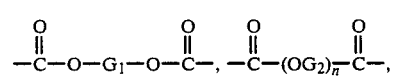

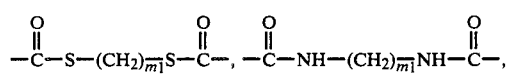

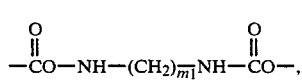

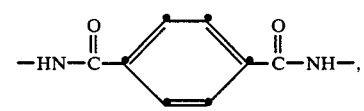

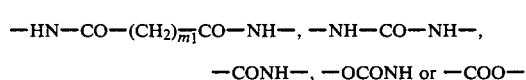

—CONH—, —OCONH or —COO—

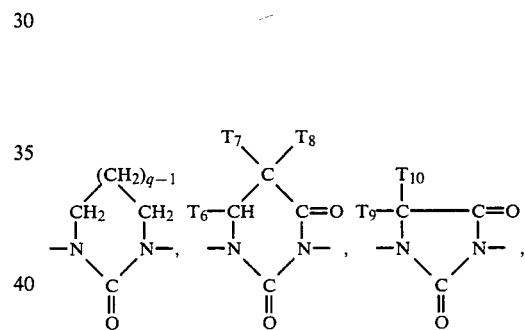

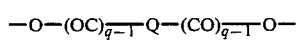

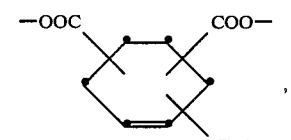

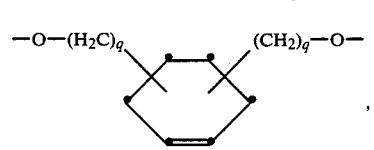

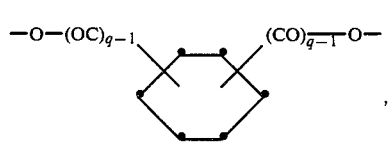

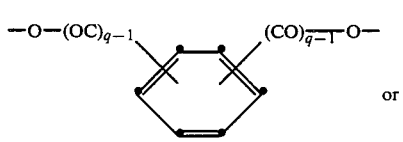

or in which $G_1$ is alkylene having 2 to 12 carbon atoms, n is an integer from 2 to 15 and $m_1$ is an integer from 2 to 12, $R_9$, $R_{10}$, $R_{11}$ and $R_{12}$ are identical to or different from one another and are phenyl, benzyl or alkyl having 1 to 4 carbon atoms, or ($R_9$ and $R_{10}$) and ($R_{11}$ and $R_{12}$), together with the nitrogen atom to which they are bonded, form a piperidine ring, $M_4$ is propionyl, acetyl or hydrogen, $A_4$ is a divalent radical of one of the formulae -continued

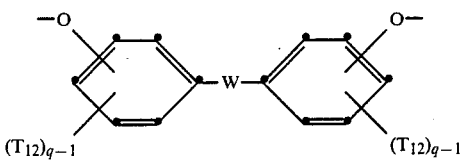

in which Q is alkylene having 2 to 8 carbon atoms, which can be interrupted by 1 or 2 oxygen atoms, W is a direct bond, —$SO_2$— or alkylene having 1 to 4 carbon atoms, $T_6$, $T_7$, $T_8$ and $T_9$ are each hydrogen or methyl, $T_{10}$ is hydrogen, methyl, ethyl or isopropyl, $T_{11}$ is methyl or ethyl, $T_{12}$ is chlorine or bromine and q is 1 or 2, and $Y_1$, $Y_2$, $T_1$, t, u and v are as defined in claim 1.

6. A process according to claim 1 wherein the ammonium salt consists essentially of cationic units of one of the formuale carbon atoms or phenylene, $t_1$ is any desired number from 1 to 3 and u is an integer from 1 to 4, $A_5$ has one of the formulae

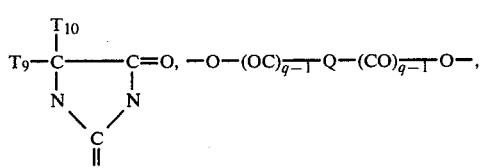

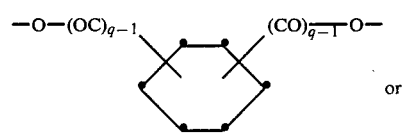

or

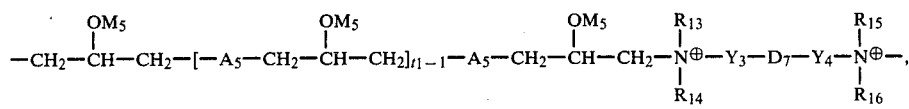

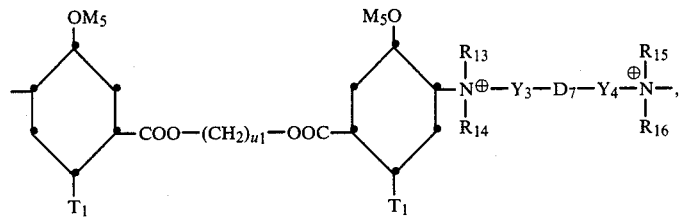

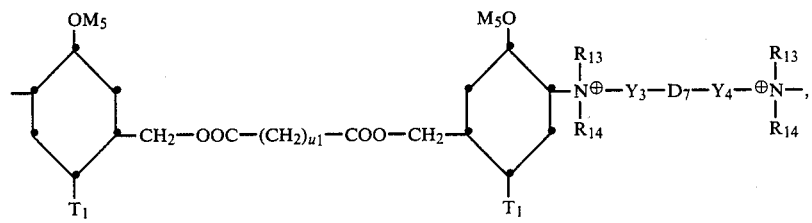

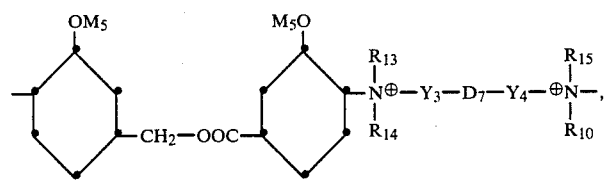

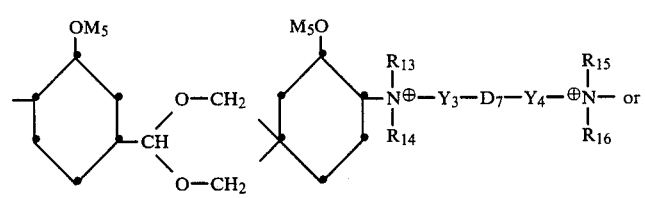

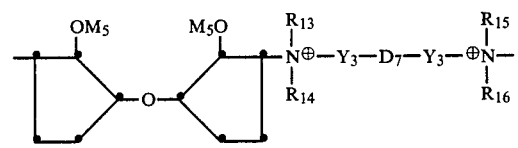

in which $R_{13}$, $R_{14}$, $R_{15}$ and $R_{16}$ are each benzyl, methyl or ethyl, or ($R_{13}$ and $R_{14}$) and ($R_{15}$ and $R_{16}$), together with the nitrogen atom to which they are bonded, form a piperidine ring, $M_5$ is acetyl or hydrogen, $T_1$ is methyl or hydrogen, $Y_3$ and $Y_4$ are each alkylene having 1 to 6

-continued

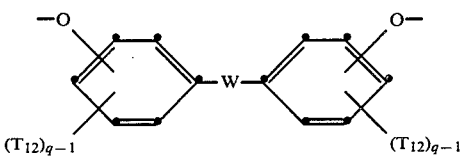

in which Q is alkylene having 2 to 8 carbon atoms, which can be interrupted by 1 or 2 oxygen atoms, W is a direct bond, —SO$_2$— or alkylene having 1 to 4 carbon atoms, T$_9$ is hydrogen or methyl, T$_{10}$ is hydrogen, methyl, ethyl or isopropyl, T$_{12}$ is chlorine or bromine and q is 1 or 2, and D$_7$ has one of the formulae

—NH—CO—NH—, —CO—NH—,

-continued

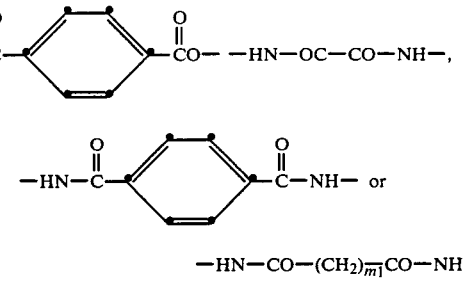

—HN—CO—(CH$_2$)$_{\overline{m_1}}$CO—NH— in which m$_1$ is an integer from 2 to 12.

7. A process according to claim 1, wherein the ammonium salt consists essentially of ionic units of the formula

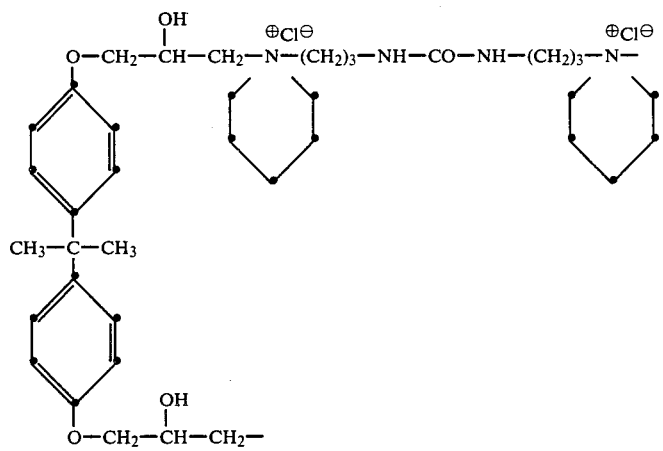

* * * * *